US012612464B2

(12) United States Patent
Sethi et al.

(10) Patent No.: US 12,612,464 B2
(45) Date of Patent: Apr. 28, 2026

(54) AUTOANTIBODY SPECIFICALLY BINDING TO NELL-1 AND ELEVATED NELL-1 POLYPEPTIDE LEVELS FOR IDENTIFYING AND TREATING MEMBRANOUS NEPHROPATHY

(71) Applicant: Mayo Foundation for Medical Education and Research, Rochester, MN (US)

(72) Inventors: Sanjeev Sethi, Rochester, MN (US); Fernando C. Fervenza, Rochester, MN (US); Benjamin J. Madden, Stewartville, MN (US); M. Cristine Charlesworth, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1032 days.

(21) Appl. No.: 17/642,773

(22) PCT Filed: Sep. 18, 2020

(86) PCT No.: PCT/US2020/051515
§ 371 (c)(1),
(2) Date: Mar. 14, 2022

(87) PCT Pub. No.: WO2021/055767
PCT Pub. Date: Mar. 25, 2021

(65) Prior Publication Data
US 2022/0389108 A1 Dec. 8, 2022

Related U.S. Application Data

(60) Provisional application No. 62/902,821, filed on Sep. 19, 2019.

(51) Int. Cl.
| | |
|---|---|
| *C07K 16/28* | (2006.01) |
| *A61K 31/196* | (2006.01) |
| *A61K 31/436* | (2006.01) |
| *A61K 38/13* | (2006.01) |
| *A61K 39/00* | (2006.01) |
| *A61P 37/06* | (2006.01) |
| *G01N 33/564* | (2006.01) |

(52) U.S. Cl.
CPC ........ *C07K 16/2887* (2013.01); *A61K 31/196* (2013.01); *A61K 31/436* (2013.01); *A61K 38/13* (2013.01); *A61P 37/06* (2018.01); *G01N 33/564* (2013.01); *A61K 39/00* (2013.01); *C07K 2317/24* (2013.01); *G01N 2800/347* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 8,361,721 B2 | 1/2013 | Copland et al. | |
| 2006/0040293 A1 | 2/2006 | Salonen et al. | |
| 2007/0210253 A1 | 9/2007 | Behar et al. | |
| 2008/0081333 A1* | 4/2008 | Mori ................... | C12Q 1/6886 |
| | | | 435/6.12 |
| 2010/0167285 A1 | 7/2010 | Schreiber et al. | |
| 2010/0196426 A1 | 8/2010 | Skog et al. | |
| 2013/0303395 A1 | 11/2013 | Lueking et al. | |
| 2017/0216244 A1 | 8/2017 | Tufro | |
| 2017/0219580 A1 | 8/2017 | Lambeau et al. | |
| 2018/0203020 A1 | 7/2018 | Esnault et al. | |
| 2019/0183969 A1 | 6/2019 | Zhu | |
| 2020/0088734 A1 | 3/2020 | Lotvall et al. | |
| 2021/0270832 A1 | 9/2021 | Charlesworth et al. | |

FOREIGN PATENT DOCUMENTS

| | | | | |
|---|---|---|---|---|
| WO | WO-2009145831 A1 * | 12/2009 | .......... | A61K 31/573 |
| WO | WO 2019/030461 | 2/2019 | | |
| WO | WO 2020/037135 | 2/2020 | | |
| WO | WO 2021/178863 | 9/2021 | | |

OTHER PUBLICATIONS

Kalantari, Biomarkers in Medicine, 2017; 11: 781-797 (Year: 2017).*
Cattran et al., Kidney International (2017) 91, 566-574 (Year: 2017).*
Kuroda et al., Biochemical and Biophysical Research Communications (1999), 265, 79-86 (Year: 1999).*
Ahn et al., "Cloning of the putative tumour suppressor gene for hereditary multiple exostoses (EXT1)," Nat. Genetics, Oct. 1, 1995, 11(2):137-143.
Alarcón, "Multiethnic lupus cohorts: what have they taught US?," Reumatol. Clinica, Dec. 23, 2010, 7(1):3-6.
Almaani et al., "Update on Lupus Nephritis," Clin. J. Am. Soc. Nephrology, Nov. 7, 2016, 12(5):825-835.
Alto et al., "Semaphorins and their Signaling Mechanisms," Methods Mol. Biology, Oct. 28, 2016, 1493:1-25.
Altschul et al., "Gapped BLAST and PSI-BLAST: a new generation of protein database search programs," Nucleic Acids Research, Sep. 1, 1997, 25(17):3389-3402.

(Continued)

*Primary Examiner* — Christina M Borgeest
(74) *Attorney, Agent, or Firm* — Grüneberg Global IP PLLC

(57) ABSTRACT

This document relates to methods and materials involved in identifying and/or treating mammals having membranous nephropathy (e.g., membranous nephropathy with an elevated level of a neural epidermal growth factor (EGF)-like 1 (NELL-1) polypeptide in the glomerular basement membrane (GBM)). For example, methods and materials for administering one or more immunosuppressive agents (e.g., corticosteroids, cyclosporine, or a B-cell reduction or depletion agent such as Rituximab) to treat a mammal (e.g., a human) having membranous nephropathy are provided.

17 Claims, 13 Drawing Sheets

Specification includes a Sequence Listing.

(56)　　　　　References Cited

OTHER PUBLICATIONS

Anders, "Nephropathic autoantigens in the spectrum of lupus nephritis," Nat. Rev. Nephrology, Jun. 13, 2019, 15(10):595-596.

Aoki et al., "The reduction of heparan sulphate in the glomerular basement membrane does not augment urinary albumin excretion," Nephrol. Dial. Transplantation, Jan. 1, 2018, 33(1):26-33.

Bajema et al., "Revision of the International Society of Nephrology/Renal Pathology Society classification for lupus nephritis: clarification of definitions, and modified National Institutes of Health activity and chronicity indices," Kidney International, Apr. 1, 2018, 93(4):789-796.

Bech et al., "Association of Anti-PLA2R Antibodies with Outcomes after Immunosuppressive Therapy in Idiopathic Membranous Nephropathy," Clin. J. Am. Soc. Nephrology, Aug. 7, 2014, 9(8):1386-1392.

Beck Jr. et al., "Membranous nephropathy: from models to man," J. Clin. Investigation, Jun. 2, 2014, 124(6):2307-2314.

Beck Jr. et al., "M-type phospholipase A2 receptor as target antigen in idiopathic membranous nephropathy," N. Engl. J. Medicine, Jul. 2, 2009, 361(1):11-21.

Beck Jr. et al., "Rituximab-Induced Depletion of Anti-PLA2R Autoantibodies Predicts Response in Membranous Nephropathy," J. Am. Soc. Nephrology, Jul. 22, 2011, 22(8):1543-1550.

Bertelli et al., "Molecular and Cellular Mechanisms for Proteinuria in Minimal Change Disease," Front. Medicine, Jun. 11, 2018, 5:170, 13 pages.

Bobart et al., "A Target Antigen-Based Approach to the Classification of Membranous Nephropathy," Mayo Clin. Proceedings, Mar. 2021, 96(3):577-591.

Borza, "Glomerular basement membrane heparan sulfate in health and disease: A regulator of local complement activation," Matrix Biology, Sep. 6, 2016, 57-58:299-310.

Brasch et al., "Thinking outside the cell: how cadherins drive adhesion," Trends Cell Biology, May 1, 2012, 22(6):299-310.

Busse et al., "Contribution of EXT1, EXT2, and EXTL3 to Heparan Sulfate Chain Elongation," J. Biol. Chemistry, Nov. 9, 2007, 282(45):32802-32810.

Busse et al., "In Vitro Polymerization of Heparan Sulfate Backbone by the EXT Proteins," J. Biol. Chemistry, Oct. 17, 2003, 278(42):41333-41337.

Busse-Wicher et al., "The extostosin family: Proteins with many functions," Matrix Biology, Apr. 2014, 35:25-33.

Chen et al., "Glomerular basement membrane and related glomerular disease," Transl. Research, Oct. 2012, 160(4):291-297.

Chen et al., "Loss of heparan sulfate glycosaminoglycan assembly in podocytes does not lead to proteinuria," Kidney International, Aug. 2008, 74(3):289-299.

Chen et al., "Podocytes require the engagement of cell surface heparan sulfate proteoglycans for adhesion to extracellular matrices," Kidney International, Dec. 1, 2010, 78(11):1088-1099.

Cook et al., "Genetic Heterogeneity in Families with Hereditary Multiple Exostoses," Am. J. Hum. Genetics, Jul. 1993, 53(1):71-79.

Couser, "Primary Membranous Nephropathy," Clin. J. Am. Soc. Nephrology, May 26, 2017, 12(6):983-997.

De Vriese et al., "A Proposal for a Serology-Based Approach to Membranous Nephropathy," J. Am. Soc. Nephrology, Oct. 24, 2016, 28(2):421-430.

Du et al., "Elevated semaphorin5A in systemic lupus erythematosus is in association with disease activity and lupus nephritis," Clin. Exp. Immunology, Feb. 17, 2017, 188(2):234-242.

Duncan et al., "The link between heparan sulfate and hereditary bone disease: finding a function for the EXT family of putative tumor suppressor proteins," J. Clin. Investigation, Aug. 2001, 108(4):511-516.

Fervenza et al., "Rituximab or Cyclosporine in the Treatment of Membranous Nephropathy," N. Engl. J. Medicine, Jul. 4, 2019, 381(1):36-46.

Frank et al., "Protocadherins," Curr. Opin. Cell Biology, Oct. 2002, 14(5):557-562.

Guan et al., "Autocrine class 3 semaphorin system regulates slit diaphragm proteins and podocyte survival," Kidney International, May 2006, 69(9):1564-1569.

Halbleib et al., "Cadherins in development: cell adhesion, sorting, and tissue morphogenesis," Genes Development, Dec. 1, 2006, 20(23):3199-3214.

Hanset et al., "Podocyte Antigen Staining to Identify Distinct Phenotypes and Outcomes in Membranous Nephropathy: A Retrospective Multicenter Cohort Study," Am. J. Kidney Diseases, Jul. 12, 2020, 76(5):624-635.

Hasebe et al., "Efficient Production and Characterization of Recombinant Human NELL1 Protein in Human Embryonic Kidney 293-F Cells," Mol. Biotechnology, Aug. 5, 2011, 51(1):58-66.

Hasebe et al., "The C-terminal region of NELL1 mediates osteoblastic cell adhesion through integrin a3ß1," FEBS Letters, Jun. 20, 2012, 586(16):2500-2506.

Herwig et al., "Thrombospondin Type 1 Domain-Containing 7A Localizes to the Slit Diaphragm and Stabilizes Membrane Dynamics of Fully Differentiated Podocytes," J. Am. Soc. Nephrology, Apr. 10, 2019, 30(5):824-839.

Hihara et al., "Anti-Phospholipase A2 Receptor (PLA2R) Antibody and Glomerular PLA2R Expression in Japanese Patients with Membranous Nephropathy," PLoS One, Jun. 29, 2016, 11(6):e0158154, 12 pages.

Huong et al., "Renal involvement in systemic lupus erythematosus. A study of 180 patients from a single center," Medicine (Baltimore), May 1999, 78(3):148-166.

Itakura et al., "Heparan sulfate is a clearance receptor for aberrant extracellular proteins," J. Cell Biology, Mar. 2, 2020, 19(3):e201911126.

Iwakura et al., "Primary Membranous Nephropathy with Enhanced Staining of Exostosin 1/Exostosin 2 in the Glomeruli: A Report of 2 Cases," Kidney Medicine, May 31, 2021, 3(4):669-673.

Kanwar et al., "Contribution of Proteoglycans Towards the Integrated Functions of Renal Glomerular Capillaries: A Historical Perspective," Am. J. Pathology, Jul. 2007, 171(1):9-13.

Kuroda et al., "Biochemical Characterization and Expression Analysis of Neural Thrombospondin-1-like Proteins NELL1 and NELL2," Biochem. Biophys. Res. Communications, Nov. 1999, 265(1):79-86.

Lee et al., "Overall and cause-specific mortality in systemic lupus erythematosus: an updated meta-analysis," Lupus, Jan. 24, 2016, 25(7):727-734.

Luce et al., "The neuronal EGF-related genes NELL1 and NELL2 are expressed in hemopoietic cells and developmentally regulated in the B lineage," Gene, Apr. 29, 1999, 231(1-2):121-126.

Makker et al., "Idiopathic membranous nephropathy: an autoimmune disease," Semin. Nephrology, Jul. 2011, 31(4):333-340.

Matshuhashi et al., "New gene, nel, encoding a M(r) 93 K protein with EGF-like repeats is strongly expressed in neural tissues of early stage chick embryos," Dev. Dynamics, Jun. 1995, 203(2):212-222.

McCarthy et al., "The Glomerular Basement Membrane as a Model System to Study the Bioactivity of Heparan Sulfate Glycosaminoglycans," Microsc. Microanalysis, Feb. 2012, 18(1):3-21.

McCormick et al., "The putative tumor suppressors EXT1 and EXT2 form a stable complex that accumulates in the Golgi apparatus and catalyzes the synthesis of heparan sulfate," Proc. Natl. Acad. Sci. USA, Jan. 18, 2000, 97(2):668-673.

Miner, "Glomerular basement membrane composition and the filtration barrier," Pediatr. Nephrology, Feb. 15, 2011, 26(9):1413-1417.

Miner, "Glomerular filtration: the charge debate charges ahead," Kidney International, Aug. 2008, 74(3):259-261.

Miner, "The glomerular basement membrane," Exp. Cell Research, Mar. 5, 2012, 318(9):973-978.

Morishita et al., "Protocadherin family: diversity, structure, and function," Curr. Opin. Cell Biology, Oct. 23, 2007, 19(5):584-592.

Nakamura et al., "Expression and regulatory effects on cancer cell behavior of NELL1 and NELL2 in human renal cell carcinoma," Cancer Science, Mar. 26, 2015, 106(5):656-664.

Nesvizhskii et al., "A Statistical Model for Identifying Proteins by Tandem Mass Spectrometry," Anal. Chemistry, Jul. 15, 2003, 75(17):4646-4658.

(56) References Cited

OTHER PUBLICATIONS

Neufeld et al., "The semaphorins and their receptors as modulators of tumor progression," Drug Resist. Updates, Aug. 28, 2016, 29:1-12.

Paulson et al., "Glycosyltransferases: Structure, localization, and control of cell type-specific glycosylation," J. Biol. Chemistry, Oct. 15, 1989, 264(3):17615-17618.

PCT International Preliminary Report on Patentability in International Appln. No. PCT/US2020/051515, dated Mar. 15, 2022, 8 pages.

PCT International Search Report and Written Opinion in International Appln. No. PCT/US2020/051515, dated Jan. 6, 2021, 11 pages.

Pourcine et al., "Prognostic value of PLA2R autoimmunity detected by measurement of anti-PLA2R antibodies combined with detection of PLA2R antigen in membranous nephropathy: A single-centre study over 14 years," PLoS One, Mar. 3, 2017, 12(3):e0173201, 18 pages.

Pozdzik et al., "Membranous Nephropathy and Anti-Podocytes Antibodies: Implications for the Diagnostic Workup and Disease Management," BioMed Res. International, Jan. 8, 2018, 2018:6281054, 19 pages.

ProteinAtlas.org [online], "NELL1—Kidney," available on or before Feb. 9, 2021 via Internet Archive: Wayback Machine URL<https://web.archive.org/web/20210209071800/https://www.proteinatlas.org/ENSG00000165973-NELL1/tissue/kidney>, retrieved on Jun. 4, 2021, retrieved from URL<https://www.proteinatlas.org/ENSG00000165973-NELL1/tissue/kidney>, 3 pages.

ProteinAtlas.org [online], "PCDH7—Kidney," available on or before Jun. 26, 2015 via Internet Archive: Wayback Machine URL<https://web.archive.org/web/20150626215650/https://www.proteinatlas.org/ENSG00000169851-PCDH7/tissue/kidney>, retrieved on Jun. 11, 2021, retrieved from URL<https://www.proteinatlas.org/ENSG00000169851-PCDH7/tissue/kidney>, 3 pages.

Raats et al., "Glomerular heparan sulfate alterations: Mechanisms and relevance for proteinuria," Kidney International, Feb. 2000, 57(2):385-400.

Ravindran et al., "In Patients with Membranous Lupus Nephritis, Exostosin-Positivity and Exostosin-Negativity Represent Two Different Phenotypes," J. Am. Soc. Nephrology, Jan. 21, 2021, 32(3):695-706.

Ravindran et al., "Proteomic Analysis of Complement Proteins in Membranous Nephropathy," Kidney Int. Reports, Jan. 30, 2020, 5(5):618-626.

Roberts et al., "Familial Nephropathy and Multiple Exostoses With Exostosin-1 (EXT1) Gene Mutation," J. Am. Soc. Nephrology, Mar. 2008, 19(3):450-453.

Ronco et al., "Pathogenesis of membranous nephropathy: recent advances and future challenges," Nat. Rev. Nephrology, Feb. 28, 2012, 8(4):203-213.

Ronco et al., "Pathophysiological advances in membranous nephropathy: time for a shift in patient's care," Lancet, May 16, 2015, 385(9981):1983-1992.

Rops et al., "Modulation of heparan sulfate in the glomerular endothelial glycocalyx decreases leukocyte influx during experimental glomerulonephritis," Kidney International, Apr. 23, 2014, 86(5):932-942.

Rosini et al., "Thrombospondin-1 promotes matrix homeostasis by interacting with collagen and lysyl oxidase precursors and collagen cross-linking sites," Sci. Signaling, May 29, 2018, 11(532):eaar2566, 16 pages.

Sano et al., "Protocadherins: a large family of cadherin-related molecules in central nervous system," EMBO Journal, Jun. 1993, 12(6):2249-2256.

Sethi et al., "Exostosin 1/Exostosin 2-Associated Membranous Nephropathy," J. Am. Soc. Nephrology, May 6, 2019, 30(6):1123-1136.

Sethi et al., "Mass Spectrometry Based Proteomic Diagnosis of Renal Immunoglobulin Heavy Chain Amyloidosis," Clin. J. Am. Soc. Nephrology, Sep. 28, 2010, 5(12):2180-2187.

Sethi et al., "Mass spectrometry based proteomics in the diagnosis of kidney disease," Curr. Opin. Nephrol. Hypertension, May 2013, 22(3):273-280.

Sethi et al., "Neural epidermal growth factor-like 1 protein (NELL-1) associated membranous nephropathy," Kidney International, Oct. 10, 2019, 97(1):163-174.

Sethi et al., "Protocadherin 7-Associated Membranous Nephropathy," J. Am. Soc. Nephrology, Apr. 8, 2021, 32(5):1249-1261.

Sethi et al., "Semaphorin 3B-associated membranous nephropathy is a distinct type of disease predominantly present in pediatric patients," Kidney International, Nov. 1, 2020, 98(5):1253-1264.

Stoddard et al., "Structure and function insights garnered from in silico modeling of the thrombospondin type-1 domain-containing 7A antigen," Proteins, Dec. 21, 2018; 87(2):136-145.

Stojan et al., "Epidemiology of systemic lupus erythematosus: an update," Curr. Opin. Rheumatology, Mar. 2018, 30(2):144-150.

Sugar et al., "N-sulfation of heparan sulfate is critical for syndecan-4-mediated podocyte cell-matrix interactions," Am. J. Physiol. Renal Physiology, Mar. 2, 2016, 310(1):F1123-F1135.

Sugar et al., "Podocyte-specific deletion of NDST1, a key enzyme in the sulfation of heparan sulfate glycosaminoglycans, leads to abnormalities in podocyte organization in vivo," Kidney International, Aug. 7, 2013, 85(2):307-318.

Takamatsu et al., "Diverse roles for semaphorin-plexin signaling in the immune system," Trends Immunology, Feb. 9, 2012, 33(3):127-135.

Tapia et al., "Semaphorin3a disrupts podocyte foot processes causing acute proteinuria," Kidney International, Dec. 12, 2007, 73(6):733-740.

Ting et al., "Human NELL-1 Expressed in Unilateral Coronal Synostosis," J. Bone Miner. Research, Jan. 1999, 14(1): 80-89.

Tomas et al., "Autoantibodies against thrombospondin type 1 domain-containing 7A induce membranous nephropathy," J. Clin. Investigation, May 23, 2016, 126(7):2519-2532.

Tomas et al., "Thrombospondin Type-1 Domain-Containing 7A in Idiopathic Membranous Nephropathy," N. Engl. J. Medicine, Nov. 13, 2014, 371(24):2277-2287.

UniProt Accession No. O60245, "Protocadherin-7," dated Jun. 7, 2017, 5 pages.

Van den Born et al., "Distribution of GBM heparan sulfate proteoglycan core protein and side chains in human glomerular diseases," Kidney International, Feb. 1993, 43(2):454-463.

Vrana et al., "Classification of amyloidosis by laser microdissection and mass spectrometry based proteomic analysis in clinical biopsy specimens," Blood, Oct. 1, 2009, 114(24):4957-4959.

Watanabe et al., "Cloning and Characterization of Two Novel Human cDNAs (NELL1 and NELL2) Encoding Proteins with Six EGF-like Repeats," Genomics, Dec. 15, 1996, 38(3):273-276.

Yazdani et al., "The semaphorins," Genome Biology, Mar. 30, 2006, 7(3):211, 14 pages.

Zaghrini et al., "Novel ELISA for thrombospondin type 1 domain-containing 7A autoantibodies in membranous nephropathy," Kidney International, Mar. 2019, 95(3):666-679.

Zhang et al., "Craniosynostosis in transgenic mice overexpressing Nell-1," J. Clin. Investigation, Sep. 2002, 110(6):861-870.

Zhang et al., "Overexpression of Nell-1, a Craniosynostosis-Associated Gene, Induces Apoptosis in Osteoblasts During Craniofacial Development," J. Bone Miner. Research, Dec. 2003, 18(12):2126-2134.

Zhang et al., "The Role of NELL-1, a Growth Factor Associated with Craniosynostosis, in Promoting Bone Regeneration," J. Dent. Research, Jul. 20, 2010, 89(9):865-878.

U.S. Appl. No. 17/254,086, filed Dec. 18, 2020, M. Cristine Charlesworth, Published as U.S. Publication No. 2021/0270832.

* cited by examiner

Ⓐ

Bio View:
2569 Proteins in 2230 Clusters
With 2568 Filtered Out

Probability Legend:

| | |
|---|---|
| over 95% | |
| 80% to 94% | |
| 50% to 79% | |
| 20% to 49% | |
| 0% to 19% | |

| Protein | Accession Number |
|---|---|
| Protein kinase C-binding protein NELL1 OS=Homo sapiens OX=9606 GN=NELL1 PE=1 SV=4 | sp | Q92832 | NELL1_HUMAN |
| Immunoglobulin gamma-1 heavy chain OS=Home sapiens OX=9606 PE=1 SV=2 | sp | P0DOX5 | IGG1_HUMAN |
| Immunoglobulin Heavy constant gamma 2 OS=Homo sapiens OX=9606 GN=IGHG2 PE=1 SV=2 | sp | P01859 | IGHG2_HUMAN |
| Immunoglobulin heavy constant gamma 3 OS=Homo sapiens OX=9606 GN=IGHG3 PE=1 S... | sp | P01860 | IGHG3_HUMAN |
| Immunoglobulin heavy constant gamma 4 OS=Homo sapiens OX=9606 GN=IGHG4 PE=1 SV=1 | sp | P01861 | IGHG4_HUMAN |
| Secretory phospholipase A2 receptor OS=Homo sapiens OX=9606 GN=PLA2R1 PE=1 SV=2 | sp | Q13018 | PLA2R_HUMAN |

| Molecular Weight | Protein Grouping Ambiguity | combined_ctrls | case_01 | case_02 | case_03 | case_04 | case_05 | case_06 |
|---|---|---|---|---|---|---|---|---|
| 90 kDa | | 0 | 78 | 91 | 35 | 60 | 42 | 73 |
| 49 kDa | ☆ | 57 | 89 | 58 | 54 | 54 | 63 | 64 |
| 36 kDa | ☆ | 44 | 84 | 49 | 38 | 23 | 75 | 35 |
| 41 kDa | ☆ | 45 | 80 | 54 | 48 | 28 | 71 | 38 |
| 36 kDa | ☆ | 22 | 35 | 22 | 20 | 37 | 29 | 70 |
| 169 kDa | ☆ | 5 | 17 | 3 | 4 | 13 | (0) | 21 |

NELL1                    IgG                    Merged

NELL-1                    IgG                    Merged

NELL-1                    IgG                    Merged

SEQUENCE LISTING

<160> NUMBER OF SEQ ID NOS: 2

<210> SEQ ID NO 1
<211> LENGTH: 810
<212> TYPE: PRT
<213> ORGANISM: Homo sapiens

<400> SEQUENCE: 1

Met Pro Met Asp Leu Ile Leu Val Val Trp Phe Cys Val Cys Thr Ala
1               5                   10                  15

Arg Thr Val Val Gly Phe Gly Met Asp Pro Asp Leu Gln Met Asp Ile
                20                  25                  30

-continued

Val Thr Glu Leu Asp Leu Val Asn Thr Thr Leu Gly Val Ala Gln Val
        35                 40                 45

Ser Gly Met His Asn Ala Ser Lys Ala Phe Leu Phe Gln Asp Ile Glu
        50                 55                 60

Arg Glu Ile His Ala Ala Pro His Val Ser Glu Lys Leu Ile Gln Leu
65                 70                 75                 80

Phe Arg Asn Lys Ser Glu Phe Thr Ile Leu Ala Thr Val Gln Gln Lys
              85                 90                 95

Pro Ser Thr Ser Gly Val Ile Leu Ser Ile Arg Glu Leu Glu His Ser
            100               105             110

Tyr Phe Glu Leu Glu Ser Ser Gly Leu Arg Asp Glu Ile Arg Tyr His
            115               120             125

Tyr Ile His Asn Gly Lys Pro Arg Thr Glu Ala Leu Pro Tyr Arg Met
        130               135                 140

Ala Asp Gly Gln Trp His Lys Val Ala Leu Ser Val Ser Ala Ser His
145                 150             155             160

Leu Leu Leu His Val Asp Cys Asn Arg Ile Tyr Glu Arg Val Ile Asp
            165               170             175

Pro Pro Asp Thr Asn Leu Pro Pro Gly Ile Asn Leu Trp Leu Gly Gln
            180               185             190

Arg Asn Gln Lys His Gly Leu Phe Lys Gly Ile Ile Gln Asp Gly Lys
            195               200             205

Ile Ile Phe Met Pro Asn Gly Tyr Ile Thr Gln Cys Pro Asn Leu Asn
        210               215                 220

His Thr Cys Pro Thr Cys Ser Asp Phe Leu Ser Leu Val Gln Gly Ile
225                 230             235             240

Met Asp Leu Gln Glu Leu Leu Ala Lys Met Thr Ala Lys Leu Asn Tyr
            245               250             255

Ala Glu Thr Arg Leu Ser Gln Leu Glu Asn Cys His Cys Glu Lys Thr
            260               265             270

Cys Gln Val Ser Gly Leu Leu Tyr Arg Asp Gln Asp Ser Trp Val Asp
            275               280             285

Gly Asp His Cys Arg Asn Cys Thr Cys Lys Ser Gly Ala Val Glu Cys
        290               295             300

Arg Arg Met Ser Cys Pro Pro Leu Asn Cys Ser Pro Asp Ser Leu Pro
305                 310             315             320

Val His Ile Ala Gly Gln Cys Cys Lys Val Cys Arg Pro Lys Cys Ile
            325               330             335

Tyr Gly Gly Lys Val Leu Ala Glu Gly Gln Arg Ile Leu Thr Lys Ser
            340               345             350

Cys Arg Glu Cys Arg Gly Gly Val Leu Val Lys Ile Thr Glu Met Cys
            355               360             365

Pro Pro Leu Asn Cys Ser Glu Lys Asp His Ile Leu Pro Glu Asn Gln
        370               375             380

Cys Cys Arg Val Cys Arg Gly His Asn Phe Cys Ala Glu Gly Pro Lys
385                 390             395             400

Cys Gly Glu Asn Ser Glu Cys Lys Asn Trp Asn Thr Lys Ala Thr Cys
            405               410             415

Glu Cys Lys Ser Gly Tyr Ile Ser Val Gln Gly Asp Ser Ala Tyr Cys
            420               425             430

Glu Asp Ile Asp Glu Cys Ala Ala Lys Met His Tyr Cys His Ala Asn
            435               440             445

Thr Val Cys Val Asn Leu Pro Gly Leu Tyr Arg Cys Asp Cys Val Pro

```
        450                455                460

Gly Tyr Ile Arg Val Asp Asp Phe Ser Cys Thr Glu His Asp Glu Cys
465                 470                 475                 480

Gly Ser Gly Gln His Asn Cys Asp Glu Asn Ala Ile Cys Thr Asn Thr
                485                 490                 495

Val Gln Gly His Ser Cys Thr Cys Lys Pro Gly Tyr Val Gly Asn Gly
                500                 505                 510

Thr Ile Cys Arg Ala Phe Cys Glu Glu Gly Cys Arg Tyr Gly Gly Thr
                515                 520                 525

Cys Val Ala Pro Asn Lys Cys Val Cys Pro Ser Gly Phe Thr Gly Ser
                530                 535                 540

His Cys Glu Lys Asp Ile Asp Glu Cys Ser Glu Gly Ile Ile Glu Cys
545                 550                 555                 560

His Asn His Ser Arg Cys Val Asn Leu Pro Gly Trp Tyr His Cys Glu
                565                 570                 575

Cys Arg Ser Gly Phe His Asp Asp Gly Thr Tyr Ser Leu Ser Gly Glu
                580                 585                 590

Ser Cys Ile Asp Ile Asp Glu Cys Ala Leu Arg Thr His Thr Cys Trp
                595                 600                 605

Asn Asp Ser Ala Cys Ile Asn Leu Ala Gly Gly Phe Asp Cys Leu Cys
                610                 615                 620

Pro Ser Gly Pro Ser Cys Ser Gly Asp Cys Pro His Glu Gly Gly Leu
625                 630                 635                 640

Lys His Asn Gly Gln Val Trp Thr Leu Lys Glu Asp Arg Cys Ser Val
                645                 650                 655

Cys Ser Cys Lys Asp Gly Lys Ile Phe Cys Arg Arg Thr Ala Cys Asp
                660                 665                 670

Cys Gln Asn Pro Ser Ala Asp Leu Phe Cys Cys Pro Glu Cys Asp Thr
                675                 680                 685

Arg Val Thr Ser Gln Cys Leu Asp Gln Asn Gly His Lys Leu Tyr Arg
                690                 695                 700

Ser Gly Asp Asn Trp Thr His Ser Cys Gln Gln Cys Arg Cys Leu Glu
705                 710                 715                 720

Gly Glu Val Asp Cys Trp Pro Leu Thr Cys Pro Asn Leu Ser Cys Glu
                725                 730                 735

Tyr Thr Ala Ile Leu Glu Gly Glu Cys Cys Pro Arg Cys Val Ser Asp
                740                 745                 750

Pro Cys Leu Ala Asp Asn Ile Thr Tyr Asp Ile Arg Lys Thr Cys Leu
                755                 760                 765

Asp Ser Tyr Gly Val Ser Arg Leu Ser Gly Ser Val Trp Thr Met Ala
                770                 775                 780

Gly Ser Pro Cys Thr Thr Cys Lys Cys Lys Asn Gly Arg Val Cys Cys
785                 790                 795                 800

Ser Val Asp Phe Glu Cys Leu Gln Asn Asn
                805                 810
```

<210> SEQ ID NO 2
<211> LENGTH: 22

-continued

```
<212> TYPE: PRT
<213> ORGANISM: Homo sapiens

<400> SEQUENCE: 2

Arg Thr Ala Cys Asp Cys Gln Asn Pro Ser Ala Asp Leu Phe Cys Cys
1               5                   10                  15

Pro Glu Cys Asp Thr Arg
            20
```

AUTOANTIBODY SPECIFICALLY BINDING TO NELL-1 AND ELEVATED NELL-1 POLYPEPTIDE LEVELS FOR IDENTIFYING AND TREATING MEMBRANOUS NEPHROPATHY

CROSS-REFERENCE TO RELATED APPLICATIONS

This application is a National Stage application under 35 U.S.C. § 371 of International Application No. PCT/US2020/051515, having an International Filing Date of Sep. 18, 2020, which claims the benefit of U.S. Provisional Application Ser. No. 62/902,821, filed Sep. 19, 2019. The disclosure of the prior applications are considered part of (and are incorporated by reference in) the disclosure of this application.

SEQUENCE LISTING

This application contains a Sequence Listing that has been submitted electronically as an ASCII text file named 07039 1933WO1 ST25.txt. The ASCII text file, created on Oct. 9, 2020, is 8 kilobytes in size. The material in the ASCII text file is hereby incorporated by reference in its entirety.

BACKGROUND

1. Technical Field

This document relates to methods and materials involved in identifying and/or treating mammals having membranous nephropathy (e.g., membranous nephropathy with an elevated level of a neural epidermal growth factor (EGF)-like 1 (NELL-1) polypeptide in the glomerular basement membrane (GBM)). For example, this document provides methods and materials for administering one or more immunosuppressive agents (e.g., corticosteroids, cyclosporine, or a B-cell reduction or depletion agent such as Rituximab) to treat a mammal (e.g., a human) having membranous nephropathy.

2. Background Information

Membranous nephropathy (MN) is the most common cause of nephrotic syndrome in Caucasian adults. It is caused by autoantibodies against target antigens in the glomerular basement membrane (GBM), and is characterized by antigen-antibody complexes that form deposits along the GBM. MN can be classified based on the target antigens phospholipase A2 receptor 1 (PLA2R) and thrombospondin type-1 domain-containing protein 7A (THSD7A). For example, MN can be classified as PLA2R-positive (70%), THSD7A-positive (1-5%), or PLA2R/THSD7A-double negative MN. In the PLA2R/THSD7A-double negative cases, the target antigen(s) remain elusive.

SUMMARY

This document provides methods and materials involved in identifying and/or treating mammals (e.g., humans) having membranous nephropathy (e.g., membranous nephropathy with an elevated level of a NELL-1 polypeptide in the GBM). For example, this document provides methods and materials for identifying a mammal (e.g., a human) having membranous nephropathy having an elevated level of a NELL-1 polypeptide in the GBM that can serve as a target antigen in membranous nephropathy. This document also provides methods and materials for identifying a mammal (e.g., a human) having membranous nephropathy that includes the presence of autoantibodies having binding specificity for a NELL-1 polypeptide. As described herein, mammals (e.g., humans) having membranous nephropathy can be identified as having an elevated level of a NELL-1 polypeptide in the GBM. In such cases, the mammal can be classified as having membranous nephropathy that includes an elevated level of a NELL-1 polypeptide in the GBM. As also described herein, mammals (e.g., humans) having membranous nephropathy can be identified as having autoantibodies having binding specificity for a NELL-1 polypeptide. In such cases, the mammal can be classified as having membranous nephropathy that includes the presence of autoantibodies having binding specificity for a NELL-1 polypeptide. Identifying mammals (e.g., humans) as having membranous nephropathy that includes an elevated level of a NELL-1 polypeptide in the GBM and/or that includes the presence of autoantibodies having binding specificity for a NELL-1 polypeptide can allow clinicians and patients to proceed with appropriate membranous nephropathy treatment options.

This document also provides methods and materials for treating membranous nephropathy. For example, a mammal (e.g., a human) having membranous nephropathy that was identified as having an elevated level of a NELL-1 polypeptide in the GBM, as having autoantibodies having binding specificity for a n NELL-1 polypeptide, or as having both an elevated level of a NELL-1 polypeptide in the GBM and autoantibodies having binding specificity for a NELL-1 polypeptide can be administered one or more immunosuppressive agents (e.g., corticosteroids, cyclosporine, or a B-cell reduction or depletion agent such as Rituximab) to reduce inflammation and/or B-cell autoantibody production. As described herein, mammals (e.g., humans) having membranous nephropathy and identified as having an elevated level of a NELL-1 polypeptide in the GBM and/or as having autoantibodies having binding specificity for a NELL-1 polypeptide have a form of membranous nephropathy that is caused by the presence of antigen-autoantibody complexes where the antigen is a NELL-1 polypeptide. In such cases, the mammal (e.g., human) can be effectively treated using one or more immunosuppressive agents (e.g., corticosteroids, cyclosporine, or a B-cell reduction or depletion agent such as Rituximab) to reduce inflammation and/or B-cell autoantibody production. Having the ability to administer one or more immunosuppressive agents to mammals (e.g., humans) (a) having membranous nephropathy and (b) identified as having an elevated level of a NELL-1 polypeptide in the GBM and/or as having autoantibodies having binding specificity for a NELL-1 polypeptide can allow clinicians and patients to treat membranous nephropathy effectively.

As also described herein, most, if not all, membranous nephropathy cases in humans are caused by autoantibodies having specificity to a polypeptide that accumulates in the GBM. Those polypeptides include NELL-1, exostosin 1 (EXT1), exostosin 2 (EXT2), PLA2R, and THS7DA. In general, the use of immunosuppressive agents such as B-cell reduction or depletion agents (e.g., Rituximab) in cases such as membranous nephropathy currently requires an identification of autoantibodies (e.g., anti-PLA2R autoantibodies or anti-THS7DA autoantibodies) before a powerful B-cell reduction or depletion agent such as Rituximab can be administered to a human to treat membranous nephropathy. Based, at least in part, on the results presented herein, however, such an identification is no longer needed prior to using an immunosuppressive agent to treat membranous nephropathy. For example, a mammal (e.g., a human) having membranous nephropathy (e.g., membranous nephropathy with an elevated level of an EXT1, an EXT2, a PLA2R, and/or a THS7DA polypeptide) can be administered one or more immunosuppressive agents (e.g., corticosteroids, cyclosporine, or a B-cell reduction or depletion agent such as Rituximab) to treat membranous nephropathy without having been tested for an elevated level of any polypeptide in the GBM and without having been tested for the presence of any autoantibody. In some cases, a mammal (e.g., a human) having membranous nephropathy can be administered one or more immunosuppressive agents (e.g., corticosteroids, cyclosporine, or a B-cell reduction or depletion agent such as Rituximab) to treat membranous nephropathy without having been tested for an elevated level of (a) an EXT1 polypeptide, (b) an EXT2 polypeptide, (c) a PLA2R polypeptide, and (d) a THS7DA polypeptide and without having been tested for the presence of (a) an autoantibody having specificity for an EXT1 polypeptide, (b) an autoantibody having specificity for an EXT2 polypeptide, (c) an autoantibody having specificity for a PLA2R polypeptide, and (d) an autoantibody having specificity for a THS7DA polypeptide. Having the ability to treat membranous nephropathy without prior testing for elevated levels of particular polypeptides in the GBM and without prior testing for the presence of particular autoantibodies can allow clinicians and patients to treat membranous nephropathy safely without the added testing delay or expense.

In some cases, identification of the target antigen and autoantibodies can be involved in the diagnosis and/or management of a mammal (e.g., a human) with membranous nephropathy. For example, a mammal (e.g., a human) having membranous nephropathy (e.g., membranous nephropathy with GBM accumulation of a NELL-1, EXT1, EXT2, PLA2R, and/or THS7DA polypeptide and the presence of autoantibodies to one or more target antigens) can be administered one or more immunosuppressive agents (e.g., corticosteroids, cyclosporine, or a B-cell reduction or depletion agent such as Rituximab) to treat membranous nephropathy. In some cases, the response to the immunosuppressive treatment can be monitored for a decrease or complete elimination of the autoantibodies to one or more of a PLA2R, THS7DA, EXT1, EXT2, or NELL-1 polypeptide. In some cases, the response to treatment can be monitored by examining a kidney biopsy for a decrease or elimination of one or more target antigens (e.g., a PLA2R, THS7DA, EXT1, EXT2, or NELL-1 polypeptide). In some cases, a mammal (e.g., a human) having membranous nephropathy can be administered one or more immunosuppressive agents (e.g., corticosteroids, cyclosporine, or a B-cell reduction or depletion agent such as Rituximab) to treat membranous nephropathy based on the presence of an autoantibody to one or more of a PLA2R, THS7DA, EXT1, EXT2, or NELL-1 polypeptide in the absence of evaluating a kidney biopsy for an elevated level of a PLA2R, THS7DA, EXT1, EXT2, or NELL-1 polypeptide. Although kidney biopsies showing an accumulation of PLA2R, THS7DA, EXT1, EXT2, and/or NELL-1 polypeptides in GBM may be considered a gold standard for diagnosis of membranous nephropathy, the presence of autoantibodies to a PLA2R, THS7DA, EXT1, EXT2, or NELL-1 polypeptide can be used to identify specific types of membranous nephropathy (e.g., membranous nephropathy associated with accumulation of PLA2R, THS7DA, EXT1, EXT2, or NELL-1 polypeptides) without the need for a kidney biopsy.

In general, one aspect of this document features methods for identifying a mammal as having membranous nephropathy including an elevated level of a polypeptide within kidney tissue of the mammal, where the polypeptide is a NELL-1 polypeptide. The methods can include, or consist essentially of, (a) determining the presence or absence of autoantibodies within the mammal, where the autoantibodies are specific for the polypeptide, (b) classifying the mammal as having the membranous nephropathy if the autoantibodies are present within the mammal, and (c) classifying the mammal as not having the membranous nephropathy if the autoantibodies are absent within the mammal. The mammal can be a human. The membranous nephropathy can lack an elevated level of an EXT1 polypeptide within the kidney tissue and can lack an elevated level of an EXT2 polypeptide within the kidney tissue. The membranous nephropathy can lack an elevated level of a PLA2R polypeptide within the kidney tissue. The membranous nephropathy can lack an elevated level of a THS7DA polypeptide within the kidney tissue. The method can include detecting the presence of the autoantibodies and classifying the mammal as having the membranous nephropathy. The method can include detecting the absence of the autoantibodies and classifying the mammal as not having the membranous nephropathy.

In another aspect, this document features methods for identifying a mammal as having kidney tissue including an elevated level of a polypeptide, where the polypeptide is a NELL-1 polypeptide. The methods can include, or consist essentially of, (a) determining the presence or absence of the kidney tissue within a sample obtained from the mammal, (b) classifying the mammal as having the kidney tissue if the presence is determined, and (c) classifying the mammal as not having the kidney tissue if the absence is determined. The mammal can be a human. The kidney tissue can lack an elevated level of an EXT1 polypeptide and the kidney tissue can lack an elevated level of an EXT2 polypeptide. The kidney tissue can lack an elevated level of a PLA2R polypeptide. The kidney tissue can lack an elevated level of a THS7DA polypeptide. The method can include detecting the presence and classifying the mammal as having the kidney tissue. The method can include detecting the absence and classifying the mammal as not having the kidney tissue.

In another aspect, this document features methods for identifying a mammal having membranous nephropathy as having autoantibodies specific for a polypeptide, where the polypeptide is a NELL-1 polypeptide. The methods can include, or consist essentially of, (a) determining the presence or absence of the autoantibodies within the mammal, (b) classifying the mammal as having the autoantibodies if the autoantibodies are present within the mammal, and (c) classifying the mammal as not having the autoantibodies if the autoantibodies are absent within the mammal. The mammal can be a human. The kidney tissue of the mammal can lack an elevated level of an EXT1 polypeptide and can lack an elevated level of an EXT2 polypeptide. The kidney tissue of the mammal can lack an elevated level of a PLA2R polypeptide. The kidney tissue of the mammal can lack an elevated level of a THS7DA polypeptide. The method can include detecting the presence and classifying the mammal as having the autoantibodies. The method can include detecting the absence and classifying the mammal as not having the autoantibodies.

In another aspect, this document features methods for treating a mammal having membranous nephropathy. The methods can include, or consist essentially of, (a) identifying a mammal as having (i) autoantibodies specific for a polypeptide or (ii) kidney tissue comprising an elevated level of the polypeptide, where the polypeptide is a NELL-1 polypeptide, and (b) administering an immunosuppressant to the mammal. The mammal can be a human. The mammal can be identified as having the autoantibodies. The mammal can be identified as having the kidney tissue. The immunosuppressant can be a B-cell inhibitor. The B-cell inhibitor can be rituximab. The immunosuppressant can be a calcineurin inhibitor. The calcineurin inhibitor can be cyclosporine or tacrolimus. The immunosuppressant can be an mTOR inhibitor. The mTOR inhibitor can be sirolimus or everolimus. The immunosuppressant can be a DNA damage inducer. The DNA damage inducer can be chlorambucil. The level of autoantibodies present within the mammal can be reduced by at least 5 percent following the administering step. The level of autoantibodies present within the mammal can be reduced by at least 25 percent following the administering step. The method level of autoantibodies present within the mammal can be reduced by at least 50 percent following the administering step.

In another aspect, this document features methods for treating a mammal having membranous nephropathy. The methods can include, or consist essentially of, administering an immunosuppressant to a mammal identified as having (i) autoantibodies specific for a polypeptide or (ii) kidney tissue comprising an elevated level of the polypeptide, where the polypeptide is a NELL-1 polypeptide. The mammal can be a human. The mammal can be identified as having the autoantibodies. The mammal can be identified as having the kidney tissue. The immunosuppressant can be a B-cell inhibitor. The B-cell inhibitor can be rituximab. The immunosuppressant can be a calcineurin inhibitor. The calcineurin inhibitor can be cyclosporine or tacrolimus. The immunosuppressant can be an mTOR inhibitor. The mTOR inhibitor can be sirolimus or everolimus. The immunosuppressant can be a DNA damage inducer. The DNA damage inducer can be chlorambucil. The level of autoantibodies present within the mammal can be reduced by at least 5 percent following the administering step. The level of autoantibodies present within the mammal can be reduced by at least 25 percent following the administering step. The level of autoantibodies present within the mammal can be reduced by at least 50 percent following the administering step.

In another aspect, this document features methods for treating a mammal having membranous nephropathy and kidney tissue including an elevated level of a polypeptide, where the polypeptide is a NELL-1 polypeptide. The methods can include, or consist essentially of, administering an immunosuppressant to the mammal. The mammal can be a human. The mammal can have autoantibodies specific for the polypeptide. The mammal can be identified as having the kidney tissue. The kidney tissue can lack an elevated level of an EXT1 polypeptide. The kidney tissue can lack an elevated level of an EXT2 polypeptide. The kidney tissue can lack an elevated level of a PLA2R polypeptide. The kidney tissue can lack an elevated level of a THS7DA polypeptide. The immunosuppressant can be a B-cell inhibitor. The B-cell inhibitor can be rituximab. The immunosuppressant can be a calcineurin inhibitor. The calcineurin inhibitor can be cyclosporine or tacrolimus. The immunosuppressant can be an mTOR inhibitor. The mTOR inhibitor can be sirolimus or everolimus. The immunosuppressant can be a DNA damage inducer. The DNA damage inducer can be chlorambucil. The level of autoantibodies present within the mammal can be reduced by at least 5 percent following the administering step. The level of autoantibodies present within the mammal can be reduced by at least 25 percent following the administering step. The level of autoantibodies present within the mammal can be reduced by at least 50 percent following the administering step.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIGS. 2A-2C. Proteomic Identification of NELL-1 in PLA2R-negative MN. Glomeruli were microdissected and analyzed using mass spectrometry as described in methods. FIG. 2A shows a glomerulus marked for dissection and vacant space on slide following microdissection. FIG. 2B shows high spectral counts of NELL-1 in 6 cases of PLA2R-negative MN. Numbers in green boxes represent spectral counts of MS/MS matches to a respective protein. All six cases show large total spectral counts for NELL-1 and immunoglobulins, baseline spectral counts of PLA2R was detected in 5 of 6 cases. For comparison, the average total spectral counts from 6 control cases (day 0 protocol transplant biopsies) are also shown. FIG. 2C shows the representative sequence coverage map of NELL-1 from 1 case. A human NELL-1 sequence is shown (SEQ ID NO:1). Amino acids highlighted in bold letters over yellow background are the amino acids detected. Green highlighted boxes indicated amino acids with artifactual chemical modification induced by mass spectrometry such as oxidation of methionine.

FIG. 4A shows bright granular capillary wall staining for NELL-1 along the glomerular basement membranes in 6 cases of NELL-1 associated MN. Note segmental capillary wall staining in case 9, FIG. 4B shows negative NELL-1 staining in control cases. There was no capillary wall staining for NELL-1 in (a-b) 2 cases of PLA2R-associated MN, (c) an additional case that was PLA2R negative but also NELL-1 negative, (d) IgA nephropathy, (e) focal segmental glomerulosclerosis (FSGS), and (f) diabetic glomerulus. Note very weak podocyte staining for NELL-1 but negative capillary wall staining. FIG. 4C IF/IHC shows bright capillary wall staining for NELL-1 of 3 cases of the French validation cohort. Case 1 (patient 30) was stained (a-b) by both IHC and IF, and the remaining 2 cases (c and d, patients 31 and 32) were stained with IF only. FIG. 4D IF shows capillary wall staining for NELL-1 of 2 cases (a-b) of the Belgian validation cohort.

FIG. 6A. Positive granular staining for NELL-1 along the GBM in 6 cases of NELL-1 associated MN. Note segmental staining in case 3 and case 13. FIG. 6B. Positive granular staining for NELL-1 along the GBM in 6 cases of NELL-1 associated MN. FIG. 6C. Positive granular staining for NELL-1 along the GBM in 6 cases of NELL-1 associated MN. FIG. 6D. Positive granular staining for NELL-1 along the GBM in 4 cases of NELL-1 associated MN.

FIGS. 7D, 7E, and 7F are enlarged images of the boxed sections in FIG. 7A, FIG. 7B, and FIG. 7C respectively. FIG. 7G shows quantitative analysis of the fluorescence recorded across sections of a representative capillary loop (arrows). Superimposition of the two signals indicates that subepithelial immune deposits contain NELL-1 (green) and IgG (red).

FIG. 8C shows the merged image. FIGS. 8D, 8E, and 8F are enlarged images of selected areas in FIGS. 8A, 8B, and 8C respectively.

FIGS. 9A and 9B shows detection of anti-NELL-1 antibodies in the serum by Western blot analysis. FIG. 9A shows reactivity of serum samples with recombinant human NELL-1 protein in 5 patients with NELL-1 associated MN. Under non reducing conditions, NELL-1 is detected predominantly as 280 kDa homodimers (bottom arrow) and 420-kDa homotrimers (top arrow) formed through a helical coiled-coil domain. In patient MN2, samples were available at the indicated time points; treatment with Rituximab was started on Jun. 14, 2017. Note lack of reactivity of sera from patients with PLA2R-associated MN, with minimal change disease (MCD), and with IgA nephropathy. Under reducing conditions NELL-1 resolves as monomeric bands of about 130 kDa, and reactivity of NELL-1 positive sera is lost suggesting that the patient's autoantibody recognize conformation-dependent epitopes. FIG. 9B shows that anti-NELL-1 autoantibodies are mainly carried by IgG1 subclass in the first patient (MN1) while IgG2 and IgG4 subtypes were also present in the second patient. This pattern corresponds to the IgG subclass immunofluorescence pattern in biopsy. FIG. 9C shows the molecular architecture of NELL-1, including an N-terminal TSP-1 like (TSPN), a coiled-coil (CC) domain, four von Willebrand factor type C (VWC) domains, and six EGF-like domains (E).

DETAILED DESCRIPTION

Figure 1:
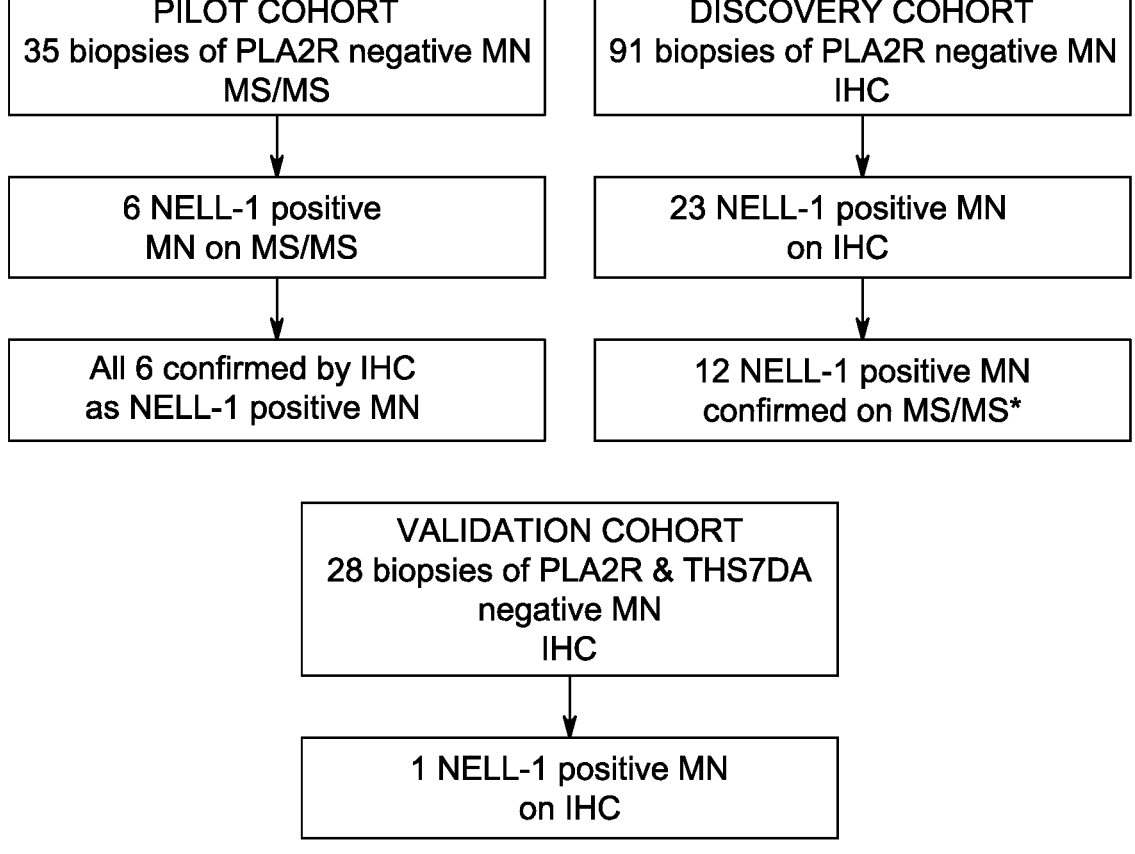
FIG. 1. Flowchart of the pilot, discovery, and validation cohorts. Initial pilot studies were done by mass spectrometry (MS) studies using 35 PLA2R negative MN. NELL-1 was detected in 6 cases which was then confirmed by immunohistochemistry (IHC). a large number (n=91) of PLA2R negative MN was studied for expression of NELL-1 by IHC (discovery cohort). This yielded an additional 23 NELL-1 positive MN cases. The positive IHC NELL-1 staining in 14 cases was confirmed by MS/MS. Two validation cohorts were studied. The first (French) validation cohort included 45 cases of PLA2R and THS7DA negative cases, of which 3 were positive for NELL-1 on IHC/immunofluorescence. The second (Belgian) validation cohort included 39 cases of PLA2R and THS7DA negative cases, of which 2 were positive for NELL-1 on immunofluorescence studies. Shaded box indicates IHC/IF study, and open box indicates MS/MS study. * MS/MS was not performed in the remaining 9 cases.

This document provides methods and materials for identifying and/or treating mammals (e.g., humans) having membranous nephropathy (e.g., membranous nephropathy with an elevated level of a NELL-1 polypeptide in the GBM). For example, this document provides methods and materials for identifying a mammal (e.g., a human) having membranous nephropathy as having (a) autoantibodies specific for a NELL-1 polypeptide and/or (b) a GBM having an elevated level of a NELL-1 polypeptide.

Any appropriate mammal having membranous nephropathy can be identified as having (a) autoantibodies specific for a NELL-1 polypeptide and/or (b) kidney tissue (e.g., GBM) having an elevated level of a NELL-1 polypeptide. In some cases, a mammal having membranous nephropathy also can have one or more other diseases or disorders (e.g., a cancer such as a lung cancer or a breast cancer). Examples of mammals having membranous nephropathy that can be identified as having (a) autoantibodies specific for a NELL-1 polypeptide and/or (b) kidney tissue (e.g., GBM) having an elevated level of a NELL-1 polypeptide as described herein include, without limitation, primates (e.g., humans and monkeys), dogs, cats, horses, cows, pigs, sheep, rabbits, mice, and rats. For example, humans having membranous nephropathy can be identified as having (a) autoantibodies specific for a NELL-1 polypeptide and/or (b) kidney tissue such as GBM having an elevated level of a NELL-1 polypeptide as described herein.

Any appropriate method can be used to determine if a mammal (e.g., a human) has autoantibodies specific for a NELL-1 polypeptide. For example, immunological assays using a NELL-1 polypeptide (or a fragment thereof capable of binding to an anti-NELL-1 antibody) can be used to determine if a sample contains autoantibodies specific for a NELL-1 polypeptide. In some cases, an immobilized NELL-1 polypeptide (or an immobilized fragment thereof) can be used to capture an anti-NELL-1 autoantibody if present within a sample being tested, and an anti-Ig antibody (e.g., an anti-human IgG antibody when testing for human autoantibodies) can be used to determine whether or not autoantibodies were captured. In some cases, an anti-Ig antibody can be labeled (e.g., fluorescently or enzymatically labeled) to aid in detection. Any appropriate sample can be used to determine if a mammal (e.g., a human) has autoantibodies specific for a NELL-1 polypeptide. For example, blood samples (e.g., whole blood samples, serum samples, and plasma samples) or urine samples obtained from a mammal being tested can be used to determine if a mammal (e.g., a human) has autoantibodies specific for a NELL-1 polypeptide.

Any appropriate method can be used to determine if a mammal (e.g., a human) has kidney tissue (e.g., GBM) having an elevated level of a NELL-1 polypeptide. For example, immunological techniques such as immunohistochemistry (IHC) techniques, immunofluorescence (IF) techniques, or Western blot techniques can be used to determine if a mammal (e.g., a human) has kidney tissue (e.g., GBM) having an elevated level of a NELL-1 polypeptide. In some cases, a kidney tissue sample obtained from a mammal to be tested can be stained using an anti-NELL-1 antibody to determine if the mammal has kidney tissue (e.g., GBM) having an elevated level of NELL-1 polypeptides. Any appropriate sample can be used to determine if a mammal (e.g., a human) has kidney tissue (e.g., GBM) having an elevated level of a NELL-1 polypeptide. For example, kidney tissue biopsies can be obtained from a mammal (e.g., a human) being tested and used to determine if a mammal (e.g., a human) has kidney tissue (e.g., GBM) having a NELL-1 polypeptide.

The term "elevated level" as used herein with respect to a NELL-1 polypeptide level refers to a level of NELL-1 polypeptides present within kidney tissue (e.g., GBM) that is greater (e.g., at least 10, 25, 35, 45, 50, 55, 65, 75, 80, 90, or 100 percent greater) than the median level of NELL-1 polypeptides present within normal kidney tissue (e.g., a normal GBM) of comparable mammals not having membranous nephropathy.

A NELL-1 polypeptide can include any appropriate amino acid sequence. An exemplary amino acid of a NELL-1 polypeptide can include, without limitation, the amino acid sequence set forth in SEQ ID NO:1 (see, e.g., FIG. 2C). In some cases, the amino acid sequence of a NELL-1 polypeptide can have a sequence that deviates from the nucleotide sequence set forth in SEQ ID NO:1, sometimes referred to as a variant sequence. For example, a NELL-1 polypeptide can have an amino acid sequence that includes one or more modifications (e.g., deletions, insertions, and substitutions) to the amino acid sequence set forth in SEQ ID NO:1. For example, an amino acid sequence of a NELL-1 polypeptide can have at least 80% sequence identity (e.g., about 82% sequence identity, about 85% sequence identity, about 88% sequence identity, about 90% sequence identity, about 93% sequence identity, about 95% sequence identity, about 97% sequence identity, about 98% sequence identity, or about 99% sequence identity) to the amino acid sequence set forth in SEQ ID NO:1. Percent sequence identity is calculated by determining the number of matched positions in aligned amino acid sequences, dividing the number of matched positions by the total number of aligned amino acids, respectively, and multiplying by 100. A matched position refers to a position in which identical amino acid occur at the same position in aligned sequences. Sequences can be aligned using the algorithm described by Altschul et al. (*Nucleic Acids Res.*, 25:3389-3402 (1997)) as incorporated into BLAST (basic local alignment search tool) programs, available at ncbi.nlm.nih.gov on the World Wide Web. BLAST searches or alignments can be performed to determine percent sequence identity between an amino acid and any other sequence or portion thereof using the Altschul et al. algorithm. BLASTN is the program used to align and compare the identity between nucleic acid sequences, while BLASTP is the program used to align and compare the identity between amino acid sequences. When utilizing BLAST programs to calculate the percent identity between an amino acid sequence and another sequence, the default parameters of the respective programs can be used. In some cases, a human NELL-1 polypeptide can have the amino acid sequence set forth in FIG. 2C.

Once a mammal (e.g., a human) having membranous nephropathy is identified as having autoantibodies specific for a NELL-1 polypeptide as described herein, the mammal can be classified as having membranous nephropathy that includes the presence of those autoantibodies (e.g., membranous nephropathy that includes the presence of anti-NELL-1 autoantibodies). In some cases, a mammal (e.g., a human) having membranous nephropathy that is identified as having autoantibodies specific for a NELL-1 polypeptide as described herein can be classified as having membranous nephropathy that includes kidney tissue having an elevated level of NELL-1 polypeptides.

Once a mammal (e.g., a human) having membranous nephropathy is identified as having kidney tissue (e.g., GBM) having an elevated level of a NELL-1 polypeptide as described herein, the mammal can be classified as having membranous nephropathy that includes the presence of that kidney tissue (e.g., membranous nephropathy that includes the presence of kidney tissue such as GBM having an elevated level of NELL-1 polypeptides). In some cases, a mammal (e.g., a human) having membranous nephropathy that is identified as having kidney tissue (e.g., GBM) having an elevated level of a NELL-1 polypeptide as described herein can be classified as having membranous nephropathy that includes autoantibodies specific for a NELL-1 polypeptide.

As described herein, this document also provides methods and materials for treating a mammal having membranous nephropathy. For example, a mammal (e.g., a human) having membranous nephropathy that is identified as having (a) autoantibodies specific for a NELL-1 polypeptide and/or (b) kidney tissue (e.g., GBM) having an elevated level of a NELL-1 polypeptide as described herein can be treated with one or more immunosuppressants. In some cases, a mammal (e.g., a human) having membranous nephropathy that is identified as having (a) autoantibodies specific for a NELL-1 polypeptide and/or (b) kidney tissue (e.g., GBM) having an elevated level of a NELL-1 polypeptide as described herein can be administered, or instructed to self-administer, one or more immunosuppressants to treat membranous nephropathy.

In some cases, a mammal (e.g., a human) having membranous nephropathy can be administered one or more immunosuppressants (e.g., anti-CD20 antibodies such as rituximab) to treat membranous nephropathy without attempting to determine if the mammal has autoantibodies specific for the following five polypeptides: a NELL-1 polypeptide, an EXT1 polypeptide, an EXT2 polypeptide, a PLA2R polypeptide, and a THS7DA polypeptide. In some cases, a mammal (e.g., a human) having membranous nephropathy can be administered one or more immunosuppressants (e.g., anti-CD20 antibodies such as rituximab) to treat membranous nephropathy without attempting to determine if the mammal has kidney tissue (e.g., GBM) having an elevated level of any of the following five polypeptides: a NELL-1 polypeptide, an EXT1 polypeptide, an EXT2 polypeptide, a PLA2R polypeptide, and a THS7DA polypeptide. In some cases, a mammal (e.g., a human) having membranous nephropathy can be administered one or more immunosuppressants (e.g., anti-CD20 antibodies such as rituximab) to treat membranous nephropathy without attempting to determine if the mammal has autoantibodies specific for those five polypeptides and without attempting to determine if the mammal has kidney tissue (e.g., GBM) having an elevated level of any of those five polypeptides. In some cases, a mammal (e.g., a human) having membranous nephropathy that is administered one or more immunosuppressants (e.g., anti-CD20 antibodies such as rituximab) to treat membranous nephropathy without attempting to determine the presence of such autoantibodies and such kidney tissue (e.g., GBM) can have autoantibodies specific for a NELL-1 polypeptide, can have autoantibodies specific for an EXT1 polypeptide, can have autoantibodies specific for an EXT2 polypeptide, can have autoantibodies specific for a PLA2R polypeptide, or can have autoantibodies specific for a THS7DA polypeptide.

Any appropriate immunosuppressant can be administered to a mammal (e.g., a human that was identified as having (a) autoantibodies specific for a NELL-1 polypeptide and/or (b) kidney tissue (e.g., GBM) having an elevated level of a NELL-1 polypeptide as described herein) to treat membranous nephropathy. In some cases, an immunosuppressant used as described herein to treat membranous nephropathy can reduce inflammation and/or reduce B-cell autoantibody production within a mammal. Examples of immunosuppressants that can be used as described herein to treat membranous nephropathy include, without limitation, mycophenolate mofetil (e.g., Cellcept); steroids such as prednisone; B-cell inhibitors such as anti-CD20 antibodies (e.g., rituximab); calcineurin inhibitors such as cyclosporine and tacrolimus; and alkylating agents/chemotherapeutic drugs such as cyclophosphamide.

In some cases, two or more (e.g., two, three, four, five, six, or more) immunosuppressants can be administered to a mammal having membranous nephropathy (e.g., a human that was identified as having (a) autoantibodies specific for a NELL-1 polypeptide and/or (b) kidney tissue (e.g., GBM) having an elevated level of a NELL-1 polypeptide as described herein). For example, two immunosuppressants (e.g., prednisone and Cellcept) can be administered to a human having membranous nephropathy.

In some cases, one or more immunosuppressants can be administered to a mammal once or multiple times over a period of time ranging from days to months. In some cases, one or more immunosuppressive drugs can be given to achieve remission of membranous nephropathy, and then given during follow up periods to prevent relapse of the membranous nephropathy. In some cases, one or more immunosuppressants can be formulated into a pharmaceutically acceptable composition for administration to a mammal (e.g., a human) having membranous nephropathy to reduce inflammation and/or to reduce B-cell autoantibody production within that mammal. For example, a therapeutically effective amount of an immunosuppressant can be formulated together with one or more pharmaceutically acceptable carriers (additives) and/or diluents. A pharmaceutical composition can be formulated for administration in solid or liquid form including, without limitation, in the form of sterile solutions, suspensions, sustained-release formulations, tablets, capsules, pills, powders, or granules.

Pharmaceutically acceptable carriers, fillers, and vehicles that can be used in a pharmaceutical composition described herein can include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

A pharmaceutical composition containing one or more immunosuppressants can be designed for oral or parenteral (including subcutaneous, intramuscular, intravenous, and intradermal) administration. When being administered orally, a pharmaceutical composition can be in the form of a pill, tablet, or capsule. Compositions suitable for parenteral administration can include aqueous and non-aqueous sterile injection solutions that can contain anti-oxidants, buffers, bacteriostats, and solutes that render the formulation isotonic with the blood of the intended recipient. The formulations can be presented in unit-dose or multi-dose containers, for example, sealed ampules and vials, and can be stored in a freeze dried (lyophilized) condition requiring the addition of the sterile liquid carrier, for example, water for injections, immediately prior to use. Extemporaneous injection solutions and suspensions can be prepared from sterile powders, granules, and tablets.

In some cases, a pharmaceutically acceptable composition including one or more immunosuppressants can be administered locally or systemically. For example, a composition provided herein can be administered locally by intravenous injection or blood infusion. In some cases, a composition provided herein can be administered systemically, orally, or by injection to a mammal (e.g., a human).

Effective doses can vary depending on the severity of the nephropathy, the route of administration, the age and general health condition of the subject, excipient usage, the possibility of co-usage with other therapeutic treatments, and the judgment of the treating physician.

An effective amount of a composition containing one or more immunosuppressants can be any amount that reduces inflammation or B-cell autoantibody production (e.g., B-cell antibody production inhibition or reduction in the number of B-cells) within a mammal having membranous nephropathy without producing significant toxicity to the mammal. For example, an effective amount of rituximab to treat membranous nephropathy as described herein can be from about 500 mg to about 1.5 g (e.g., from about 500 mg to about 1.25 g, from about 500 mg to about 1.0 g, from about 500 mg to about 750 mg, from about 750 mg to about 1.5 g, from about 1 g to about 1.5 g, or from about 1.25 g to about 1.5 g) administered IV about two weeks apart. In some cases, an effective amount of rituximab to treat membranous nephropathy as described herein can be from about 200 mg/m$^2$ to about 500 mg/m$^2$ (e.g., from about 200 mg/m$^2$ to about 450 mg/m$^2$, from about 200 mg/m$^2$ to about 400 mg/m$^2$, from about 200 mg/m$^2$ to about 375 mg/m$^2$, from about 250 mg/m$^2$ to about 500 mg/m$^2$, from about 300 mg/m$^2$ to about 500 mg/m$^2$, from about 350 mg/m$^2$ to about 500 mg/m$^2$, or from about 350 mg/m$^2$ to about 400 mg/m$^2$) administered weekly for about four weeks. If a particular mammal fails to respond to a particular amount, then the amount of an immunosuppressant can be increased by, for example, two fold. After receiving this higher amount, the mammal can be monitored for both responsiveness to the treatment and toxicity symptoms, and adjustments made accordingly. For example, levels of anti-EXT1 and/or EXT2 autoantibodies present within the mammal (e.g., within the blood of the mammal) can be monitored by an appropriate method (e.g., ELISA). In some cases, the effective amount of a composition containing one or more immunosuppressants can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition can require an increase or decrease in the actual effective amount administered.

The frequency of administration of one or more immunosuppressants can be any amount that reduces inflammation or B-cell autoantibody production (e.g., B-cell antibody production inhibition or reduction in the number of B-cells) within a mammal having membranous nephropathy without producing significant toxicity to the mammal. For example, the frequency of administration of an immunosuppressant can be from about once a day to about once a month (e.g., from about once a week to about once every other week). The frequency of administration of one or more immunosuppressants can remain constant or can be variable during the duration of treatment. A course of treatment with a composition containing one or more immunosuppressants can include rest periods. For example, a composition containing one or more immunosuppressants can be administered daily over a two-week period followed by a two-week rest period, and such a regimen can be repeated multiple times. As with the effective amount, various factors can influence the actual frequency of administration used for a particular application. For example, the effective amount, duration of treatment, use of multiple treatment agents, route of administration, and severity of the condition may require an increase or decrease in administration frequency.

An effective duration for administering a composition containing one or more immunosuppressants can be any duration that reduces inflammation or B-cell autoantibody production (e.g., B-cell antibody production inhibition or reduction in the number of B-cells) within a mammal having membranous nephropathy without producing significant toxicity to the mammal. In some cases, the effective duration can vary from several days to several months. In general, the effective duration for administering a composition containing one or more immunosuppressants to treat membranous nephropathy can range in duration from about one month to about five years (e.g., from about two months to about five years, from about three months to about five years, from about six months to about five years, from about eight months to about five years, from about one year to about five years, from about one month to about four years, from about one month to about three years, from about one month to about two years, from about six months to about four years, from about six months to about three years, or from about six months to about two years). In some cases, the effective duration for administering a composition containing one or more immunosuppressants to treat membranous nephropathy can be for as long as the mammal is alive. Multiple factors can influence the actual effective duration used for a particular treatment. For example, an effective duration can vary with the frequency of administration, effective amount, use of multiple treatment agents, route of administration, and severity of the condition being treated.

In some cases, a course of treatment and/or the severity of one or more symptoms related to membranous nephropathy can be monitored. Any appropriate method can be used to determine whether or not membranous nephropathy is being treated. For example, immunological techniques (e.g., ELISA) can be performed to determine if the level of autoantibodies (e.g., anti-NELL-1 autoantibodies, anti-EXT1 autoantibodies, anti-EXT2 autoantibodies, anti-PLA2R autoantibodies, or anti-THS7DA autoantibodies) present within a mammal being treated as described herein is reduced following the administration of one or more immunosuppressants. Remission and relapse of the disease can be monitored by testing for one or more markers for membranous nephropathy. In some cases, remission can be ascertained by detecting the disappearance or reduction of autoantibodies to NELL-1, THS7DA, PLA2R, EXT1, or EXT2 in the sera. In some cases, relapse of membranous nephropathy can be ascertained by a reappearance or elevation of autoantibodies to NELL-1, THS7DA, PLA2R, EXT1, or EXT2 in the sera.

The invention will be further described in the following examples, which do not limit the scope of the invention described in the claims.

EXAMPLES

Example 1: NELL-1 Associated Membranous Nephropathy

This Example evaluates patients having PLA2R/THSD7A-double negative MN to identify NELL-1 as a target antigen of MN, and characterize NELL-1-positive MN as a distinct type of primary MN.

Patients and Sample Collection

Biopsies were received in the Renal Pathology Laboratory, Department of Laboratory Medicine and Pathology, Mayo Clinic, for diagnosis and interpretation. Light microscopy, immunofluorescence microscopy including PLA2R studies, and electron microscopy was performed in each case of MN. The clinical information was obtained from the accompanying charts. For control cases, MS/MS was performed on 111 cases that included 15 cases of time 0 kidney transplant biopsies, 17 cases of minimal change disease, 44 cases of focal segmental glomerulosclerosis, 7 cases of diabetic glomerulosclerosis, 5 cases of IgA nephropathy, and 23 cases of PLA2R-associated MN. For control IHC, 20 cases were used that included: 4 cases of focal segmental glomerulosclerosis, 4 cases of IgA nephropathy, 4 cases of diabetes and 8 cases of PLA2R-associated MN.

Validation Cohorts

Two validation cohorts were used.

1. French cohort: Twenty-three unstained, blinded kidney biopsy slides of formalin fixed paraffin embedded (FFPE) tissue were provided by Inserm UMR-S1155 (Tenon Hospital, Paris) and analyzed in the Pathology Research Core (Mayo Clinic) by IHC for NELL-1. All 22 cases were PLA2R and THS7DA-negative MN. An additional 22 cases (FFPE) of PLA2R and THS7DA-negative MN were stained for NELL-1 at Inserm UMR-S1155 using immunofluorescence methodology.

2. Belgian Cohort: Thirty-nine unstained, blinded kidney biopsy slides of FFPE tissue of PLA2R and THS7DA-negative MN were obtained in the UCLouvain Kidney Disease Network. These cases were stained for NELL-1 at Inserm UMR-S1155 using immunofluorescence.

Protein Identification by Laser Capture Microdissection, Trypsin Digestion, Nano-LC Orbitrap Tandem Mass Spectrometry (MS/MS)

For each case 10 micron (μm) thick FFPE sections were obtained and mounted on a special PEN membrane laser microdissection slide and using a Zeiss Palm Microbean microscope, the glomeruli were microdissected to reach approximately 250-500,000 $\mu m^2$ per case.

TABLE 1

| Mass spectrometry dissections | |
| --- | --- |
| Case | Area dissected (square microns) |
| 1 | 555630 |
| 2 | 292896 |
| 3 | 501849 |

TABLE 1-continued

| Mass spectrometry dissections | |
| --- | --- |
| Case | Area dissected (square microns) |
| 4 | 498319 |
| 5 | 95355 |
| 6 | 537334 |
| 7 | 82235 |
| 8 | 403967 |
| 9 | 529081 |
| 10 | 514395 |
| 11 | 229522 |
| 12 | 529260 |
| 13 | 290584 |
| 14 | 277148 |
| 15 | 529372 |
| 16 | 518214 |
| 17 | 528766 |
| 18 | 526196 |
| 19 | 405347 |
| 20 | 263306 |

Resulting FFPE fragments were digested with trypsin and collected for MS/MS analysis. The trypsin digested peptides were identified by nano-flow liquid chromatography electrospray tandem MS/MS (nanoLC-ESI-MS/MS) using a Thermo Scientific Q-Exactive Mass Spectrometer (Thermo Fisher Scientific, Bremen, Germany) coupled to a Thermo Ultimate 3000 RSLCnano HPLC system. All MS/MS samples were analyzed using Mascot and X! Tandem set up to search a Swissprot human database. Scaffold (version 4.8.3, Proteome Software Inc., Portland, OR) was used to validate MS/MS based peptide and protein identifications. Peptide identifications were accepted at greater than 95.0% probability by the Scaffold Local FDR algorithm with protein identifications requiring a 2 peptide minimum and a 95% probability using Protein Prophet.

Laser Microdissection and Mass Spectrometry

FFPE renal biopsy materials were sent to the Mayo Clinic renal biopsy laboratory for diagnosis of membranous nephropathy. For each case, 10 μM thick paraffin sections were obtained and mounted on PEN membrane laser microdissection slides. The sections were deparaffinized using xylene and alcohol. Using a Zeiss Palm Microbean microscope and Robopalm software, multiple glomeruli were microdissected to reach approximately 250-500,000 μm² per case, and catapulted into 35 μl of digest buffer (100 mM Tris, pH 8.5/0.002% Zwittergent Z3-16) in the cap of a 0.5 ml tube. The tube was removed from the collection plate and spun at 14000 g×2 minutes. The samples were frozen until all samples were collected. Upon thawing, samples were heated to 98° C., then proteins were reduced and alkylated by sequential addition of TCEP (Tris(2-carboxyethyl) phosphine hydrochloride) and iodoacetamide to 10 mM for 30 minutes each. Trypsin (0.05 μg) was added to each tube and proteins were digested overnight at 37° C. for 16-18 hours. After digestion, the samples were acidified with trichloroacetic acid, dried down and resolubilized with A solvent for mass spectrometry.

The trypsin digested peptides were identified by nano-flow liquid chromatography electrospray tandem mass spectrometry (nanoLC-ESI-MS/MS) using a Thermo Scientific Q-Exactive Mass Spectrometer (Thermo Fisher Scientific, Bremen, Germany) coupled to a Thermo Ultimate 3000 RSLCnano HPLC system. The peptide mixture was loaded onto a 250n1 OPTI-PAK trap (Optimize Technologies, Oregon City, OR) custom packed with Michrom Magic C 8, 5 μm solid phase (Michrom Bioresources, Auburn, CA).

Chromatography was performed using 0.2% formic acid in both the A solvent (98% water/2% acetonitrile) and B solvent (80% acetonitrile/10% isopropanol/10% water), and a 5% B to 40% B gradient over 90 minutes at 400 μl/minute through a PicoFrit (New Objective, Woburn, MA) 100 μm×35 cm column handpacked with Agilent Poroshell 120 EC C18 packing. The Q-Exactive mass spectrometer experiment was a data dependent set up with the MS1 survey scan from 340-1500 m/z at resolution 70,000 (at 200 m/z), followed by HCD MS/MS scans on the top 15 ions having a charge state of +2, +3, or +4, at resolution 17,500. The ions selected for MS/MS were placed on an exclusion list for 30 seconds. The MS1 AGC target was set to 1e6 and the MS2 target is set to 1e5 with max ion inject times of 50 ms for both.

Database Searching

Tandem mass spectra was extracted by msconvert version 3.0.9134. Charge state deconvolution and deisotoping was not performed. All MS/MS samples were analyzed using Mascot (Matrix Science, London, UK; version 2.4.0) and X! Tandem (The GPM, thegpm.org; version X!Tandem Sledgehammer (2013.09.01.1)). Mascot and X! Tandem were set up to search a Swissprot human database with reverse decoy (40570 entries) assuming the digestion enzyme strict trypsin and with a fragment ion mass tolerance of 0.020 Da and a parent ion tolerance of 10.0 PPM. Glu->pyro-Glu of the n-terminus, ammonia-loss of the n-terminus, gln->pyro-Glu of the n-terminus, oxidation of methionine is specified in X! Tandem as variable modifications and carbamidomethyl of cysteine was specified as a fixed modification. Oxidation of methionine and carbamidomethyl of cysteine were specified in Mascot as variable modifications and fixed modifications respectively.

Criteria for Protein Identification

Scaffold (version Scaffold 4.8.3, Proteome Software Inc., Portland, OR) was used to validate MS/MS based peptide and protein identifications. Peptide identifications were accepted if they could be established at greater than 95.0% probability by the Scaffold Local FDR algorithm. Protein identifications were accepted if they could be established at greater than 95.0% probability and contained at least 2 identified peptides. Protein probabilities were assigned by the Protein Prophet algorithm. The protein decoy false discovery rate (FDR) was <1.5. In general, over 1500-2500 proteins were identified in each sample. Proteins that contain similar peptides and cannot be differentiated based on MS/MS analysis alone were grouped to satisfy the principles of parsimony. Proteins sharing significant peptide evidence were grouped into clusters. Protein comparisons were made with ratios of Scaffold normalized total spectral counts. The 'Spectra' value indicates the total number of mass spectrum collected on the mass spectrometer and matched to the protein using the proteomics software. A higher number of mass spectra is indicative of greater abundance and will typically yield greater amino acid sequence coverage. A higher mass spectra value also indicates a higher confidence in the protein identification.

Immunohistochemical (IHC), Immunofluorescence and Co-Localization Staining for NELL-1

Tissue sectioning and IHC staining was performed at the Pathology Research Core (Mayo Clinic, Rochester, MN) using the Leica Bond RX stainer (Leica). FFPE tissues were sectioned at 5 μm and IHC staining was performed on-line. Slides for the NELL-1 stain were retrieved for 20 minutes using Epitope Retrieval 2 (EDTA; Leica) and incubated in Protein Block (Dako) for 5 minutes. The NELL-1 primary antibody (Rabbit Polyclonal, Sigma #HPA051535) was diluted to 1:100 in Background Reducing Diluent (Dako) and incubated for 15 minutes. The detection system used was Polymer Refine Detection System (Leica). This system includes the hydrogen peroxidase block, post primary and polymer reagent, DAB, and Hematoxylin. Immunostaining visualization was achieved by incubating slides 10 minutes in DAB and DAB buffer (1:19 mixture) from the Bond Polymer Refine Detection System. To this point, slides were rinsed between steps with 1× Bond Wash Buffer (Leica). Slides were counterstained for five minutes using Schmidt hematoxylin and molecular biology grade water (1:1 mixture), followed by several rinses in 1× Bond wash buffer and distilled water, this is not the hematoxylin provided with the Refine kit. Once the immunochemistry process was completed, slides were removed from the stainer and rinsed in tap water for five minutes. Slides were dehydrated in increasing concentrations of ethyl alcohol and cleared in 3 changes of xylene prior to permanent cover slipping in xylene-based medium.

Immunofluorescence staining was performed on FFPE sections retrieved for 30 minutes using target retrieval solution high pH (Dako) in pressure cooker equipment (BioSB). The NELL-1 primary antibody (rabbit polyclonal, Atlas antibodies) was diluted to 1:100 in blocking solution (2% calf fetal serum and 2% normal goat serum) and incubated overnight at 4° C. with retrieved biopsy sections. Next, the slides were incubated with secondary antibody goat Alexa 488-conjugated anti-rabbit Fab IgG (Life technologies). Anti-human IgG Alexa Fluor 647 rabbit monoclonal antibody (Sigma) was then reacted with the retrieved tissue as described above. Finally slides were mounted in mounted medium (Thermo Scientific) and covered with LDS2460EP cover glass slides. Co-localization of NELL-1 and IgG along the glomerular basement membrane was examined by confocal microscopy using a Leica TCS-SP2 and analyzed with Leica Confocal Software version 2.61, Wetzlar, Germany.

Western Blot Analysis

The protein sample, recombinant human NELL-1 (R&D Systems) was diluted with non-reducing or reducing Laemmli sample buffer (Bio-Rad) and boiled for 5 minutes. Samples were loaded into Criterion 4-15% TGX gels (Bio-Rad) and electrophoresed in Tris-glycine-SDS running buffer. Proteins were transferred to poly (vinylidene difluoride) membranes according to standard protocols and the membranes were blocked with Pierce Protein-Free Blocking buffer (Thermo Scientific). Membranes were incubated overnight at 4° C. with sera from patients, controls (dilution 1:50) and rabbit polyclonal antibodies (dilution 1:500) against NELL-1 (Abcam). Subsequently, blots were washed and incubated for 2 hours at room temperature with goat-anti human or goat anti-rabbit IgG, AP conjugate (Sigma). Immunoreactive proteins were visualized with BCIP/NBT liquid substrate system (Sigma).

For subclass detection in non-reducing conditions, blots were incubated with mouse monoclonal anti-human IgG subclass antibodies (Southern Biotech), then revealed with alkaline phosphatase-conjugated polyclonal anti-mouse IgG antibody (Vector labs, Burlingame, CA, USA).

Patient and Biopsy Collection 35 cases (pilot cohort) of PLA2R-negative MN on kidney biopsy were selected for analysis by tandem mass spectrometry (MS/MS), and NELL-1 protein was detected in 6 cases. The 35 cases of the pilot MS/MS and 91 additional PLA2R-negative MN cases were then analyzed by immunohistochemistry (IHC) for NELL-1 staining (discovery cohort). IHC confirmed the 6 positive NELL-1 cases of the pilot cohort and detected an additional 23 cases of NELL-1, bringing the total of NELL-1 positive cases to 29 (FIG. 1). MS/MS was performed in 14 available samples of the 23 additional IHC NELL-1 positive cases from the discovery cohort to confirm the presence of NELL-1.

Mass Spectrometry (NIS/MS) Detection of NELL-1 in PLA2R-Negative Biopsies

Figure 2A:
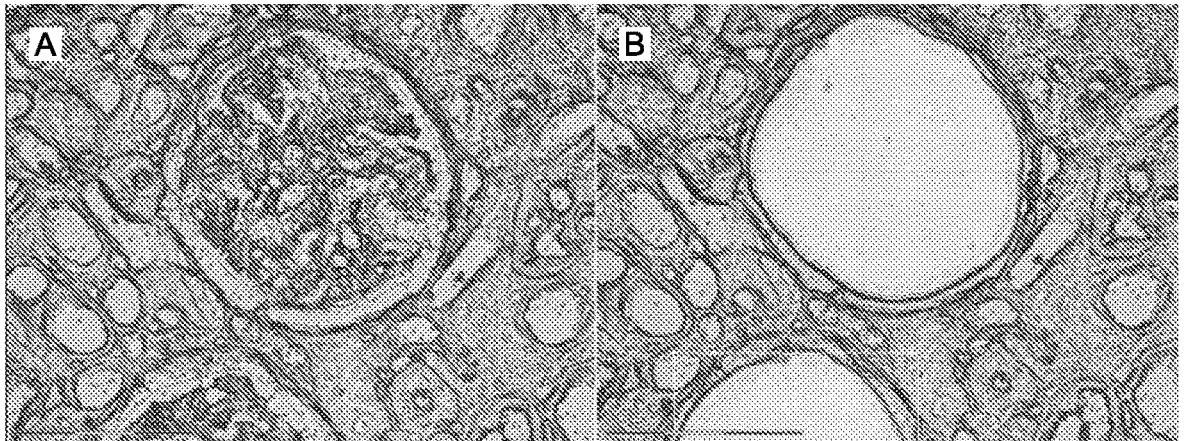
Figure 2C:
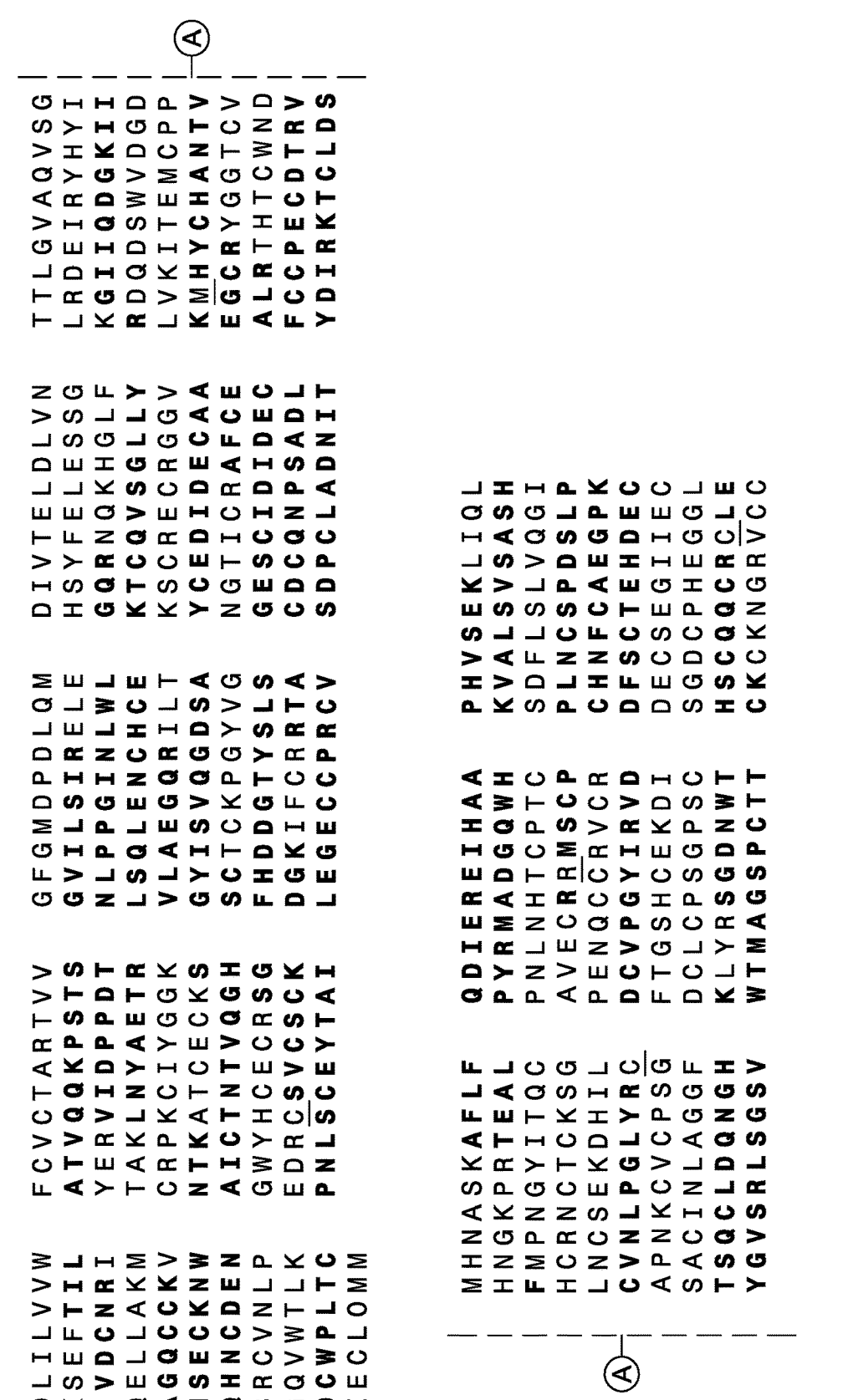
Figure 3:
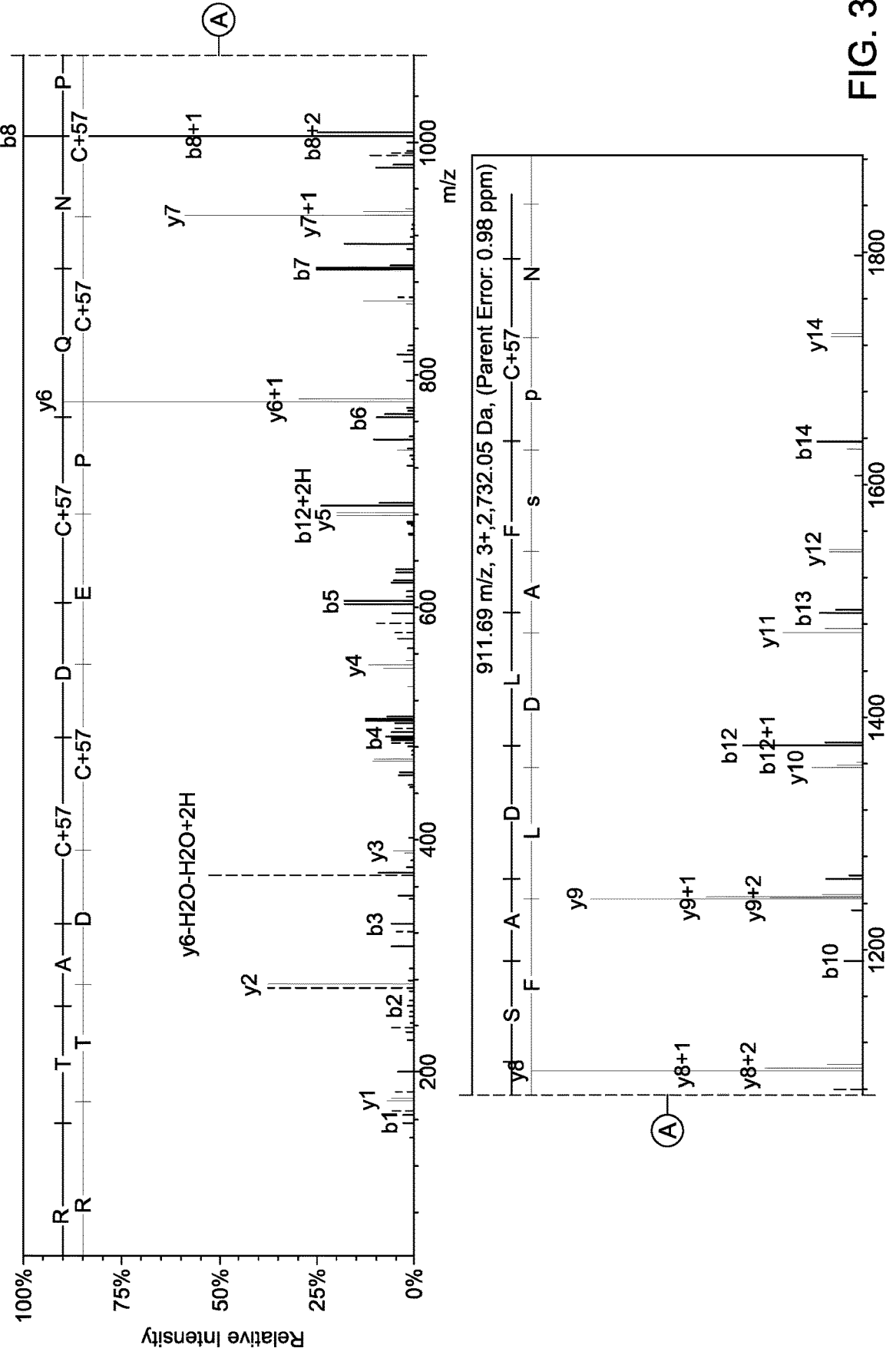
FIG. 3. An example of MS/MS spectra match to a sequence from NELL-1. The MS/MS spectra figure from Scaffold viewer of ion 911.69 $[M+3H]^{3+}$ highlighting the detected b-ions (red) and y-ions (blue) matching the theoretical fragment masses listed in the table for the NELL-1 peptide RTACDCQNPSADLFCCPECDTR (SEQ ID NO:2). The C+57 indicates the addition from alkylating with iodoacetamide. There is another R before the R in the NELL-1 sequence, indicating that this peptide has one missed trypsin cleavage site.

Glomeruli were dissected (FIG. 2A) and MS/MS studies from 35 PLA2R-negative MN cases (pilot cohort) detected the unique protein NELL-1 in in 6 cases of the pilot cohort (FIG. 2B). The average total spectral count for NELL-1 was 63.1 (S.D±21.6) per case and is comparable to total spectral counts of PLA2R (86.1, S.D±27.5) and EXT1/EXT2 (EXT1 65.3, S.D±34.6, EXT2 83.4, S.D±38.4) in PLA2R-associated and EXT1/EXT2-associated MN, respectively. All controls including PLA2R-associated MN cases were negative for NELL-1. MS/MS showed baseline spectral counts of PLA2R (average 9.6, S.D.±8.6) in NELL-1-associated MN. The spectral counts of NELL-1 in the 6 cases, along with representative sequence coverage map of NELL-1 from one case are shown in FIG. 2B-C. MS/MS was subsequently performed in 14 of 23 cases of the discovery cohort cases that were positive for NELL-1 by IHC. All cases showed similar high spectral counts of NELL-1 (FIG. 2B). An example of MS/MS spectra match to a sequence from NELL-1 is shown in FIG. 3.

All four classes of immunoglobulins (Ig) were detected in NELL-1 associated MN: IgG1 was the most abundant Ig (average 63.6, S.D±13.1), followed by IgG3 (average 53.2, S.D±19.6), IgG2 (average 50.6, S.D±23.9), and IgG4 (average 35.5, S.D±18.2).

Immunohistochemical Staining for NELL-1 in PLA2R-Negative Biopsies

Figure 4A:
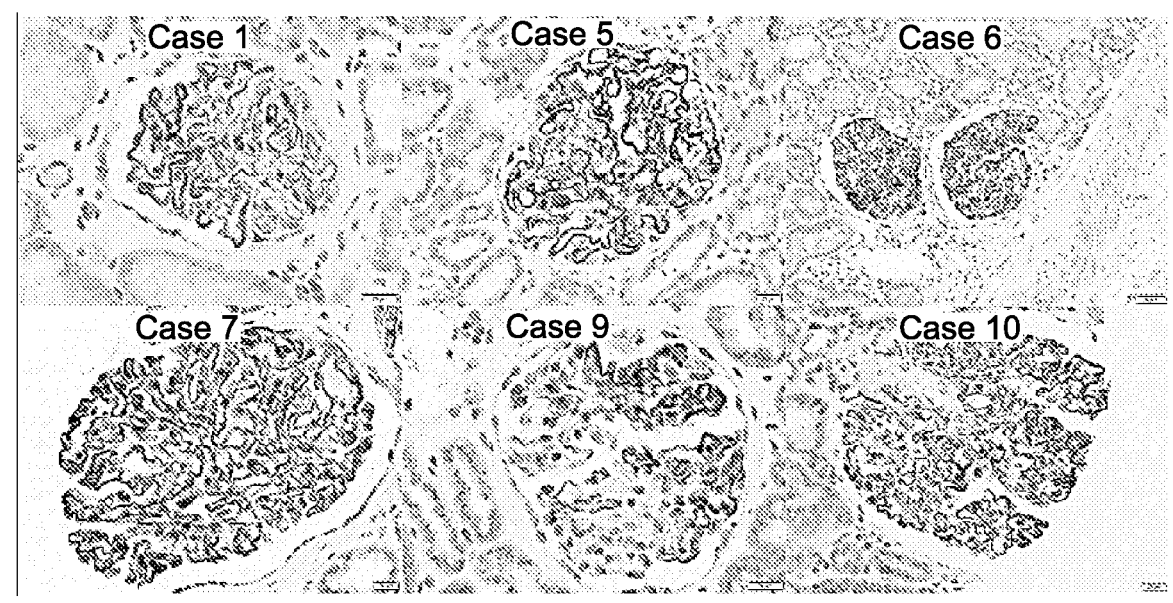
FIGS. 4A-4D. Immunohistochemical stain for NELL-1 in NELL-1-associated MN, PLA2R-associated MN, and control cases.
Figure 4B:
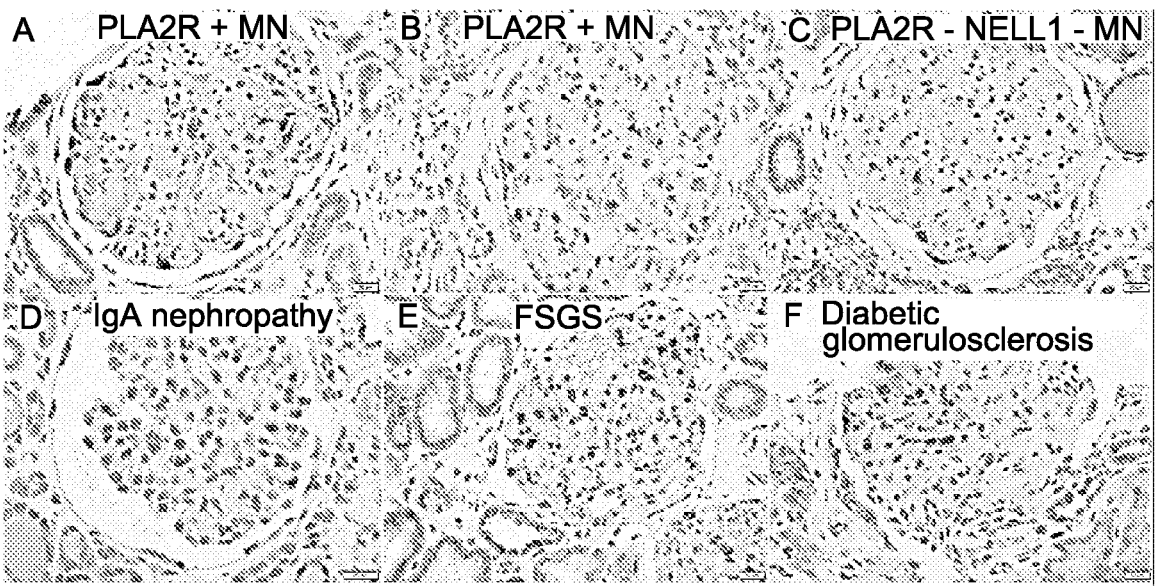
Figure 5:
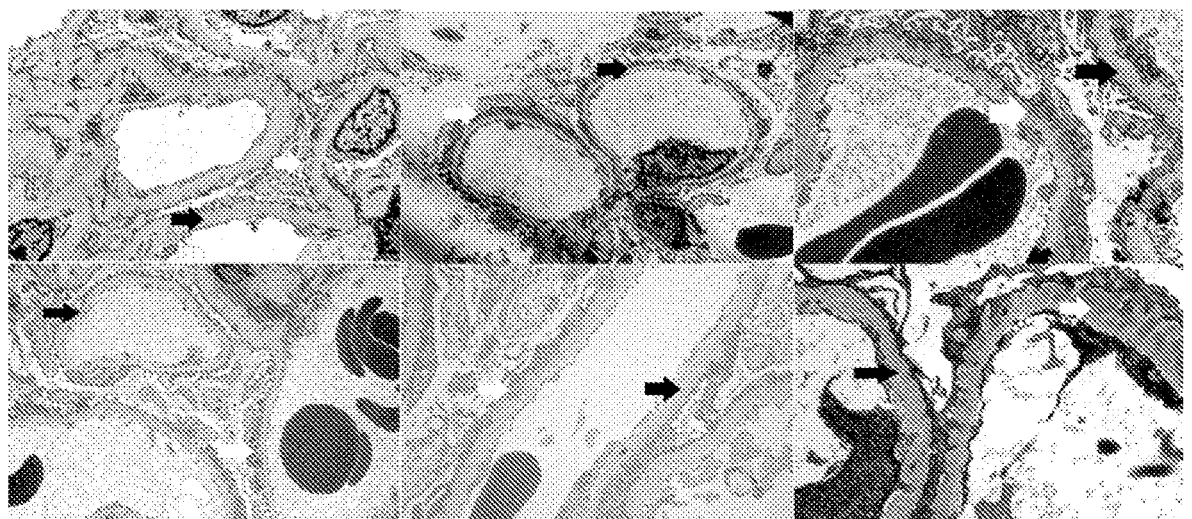
FIG. 5. Electron microscopy showing segmental subepithelial electron dense deposits in 6 cases: Black arrow points to capillary loops with no deposits, and white arrow points to subepithelial deposits. Each panel is a representative figure from one case.
Figure 6A:
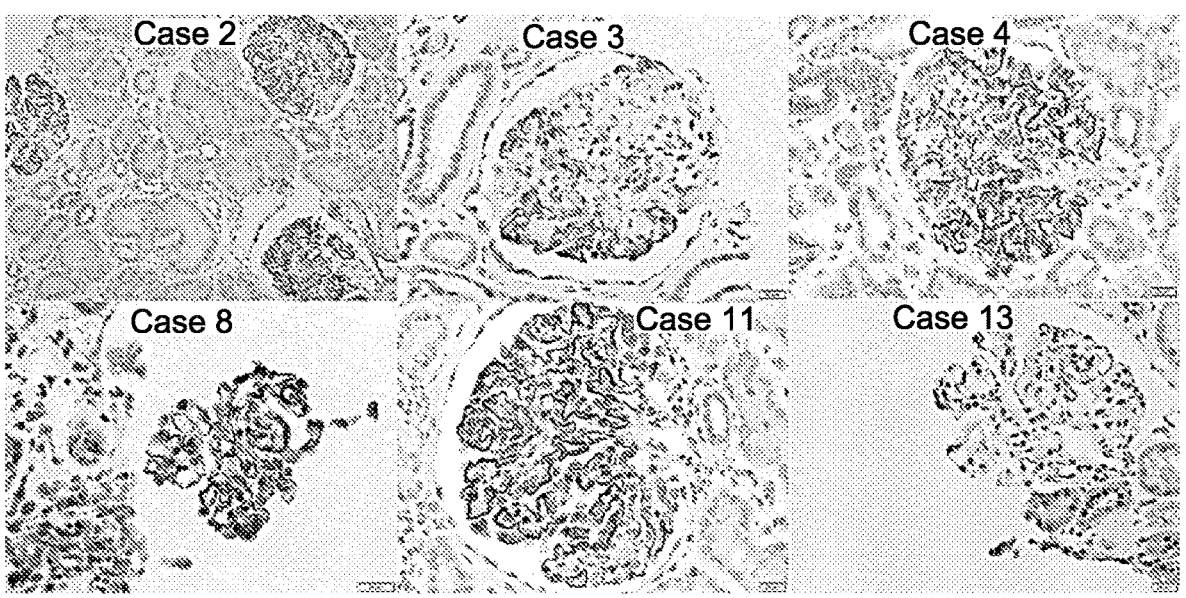
FIGS. 6A-6D. IHC staining for NELL-1.
Figure 6B:
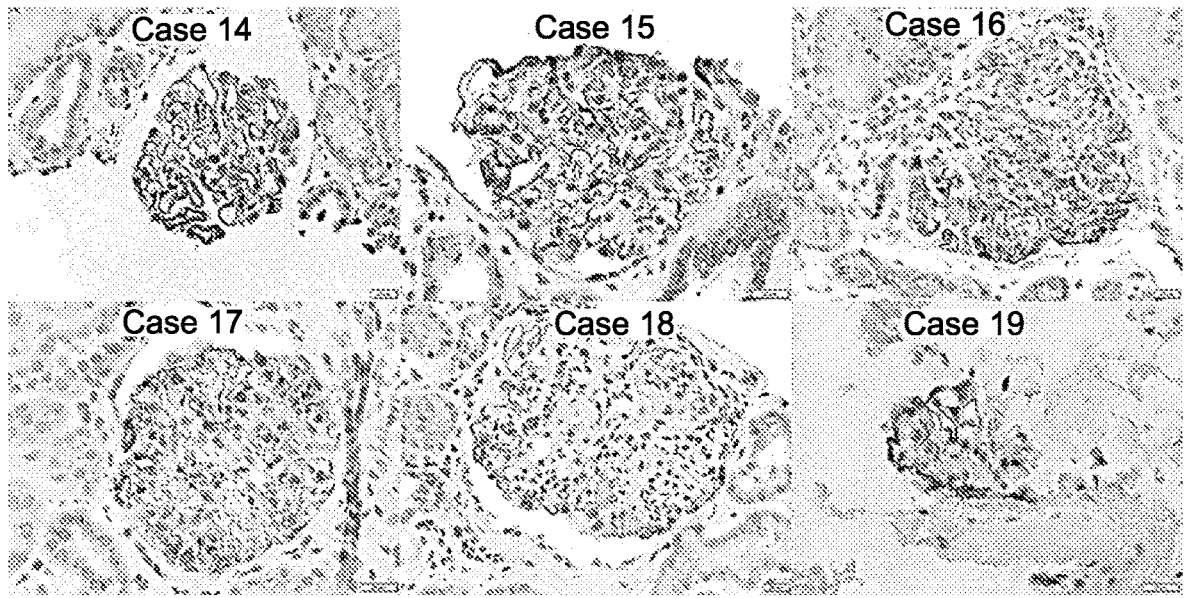
Figure 6C:
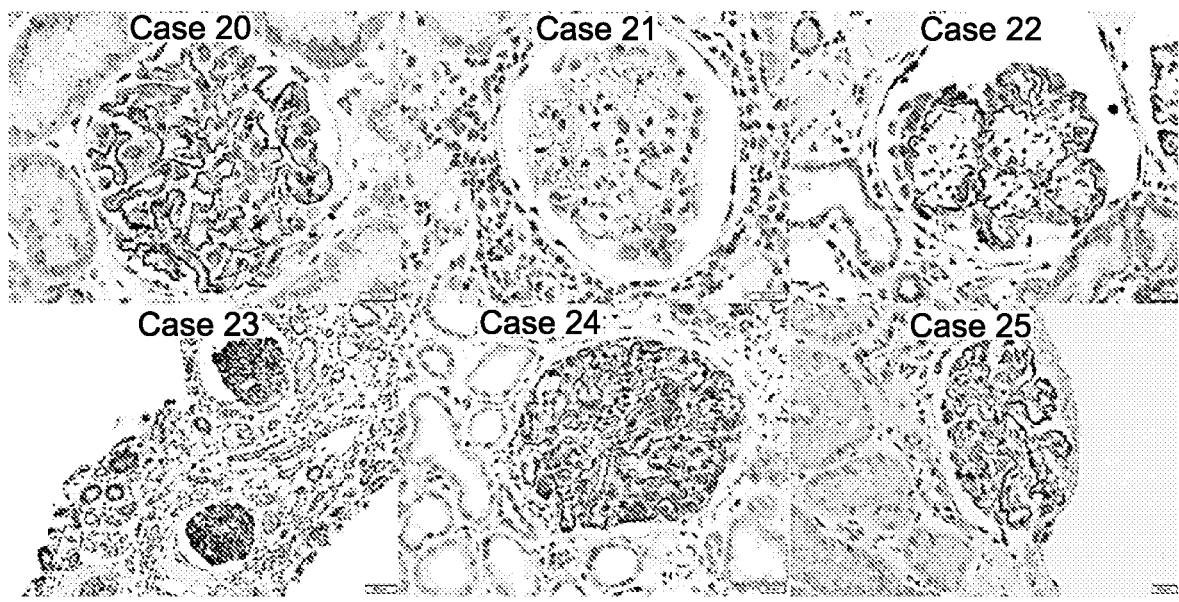
Figure 6D:
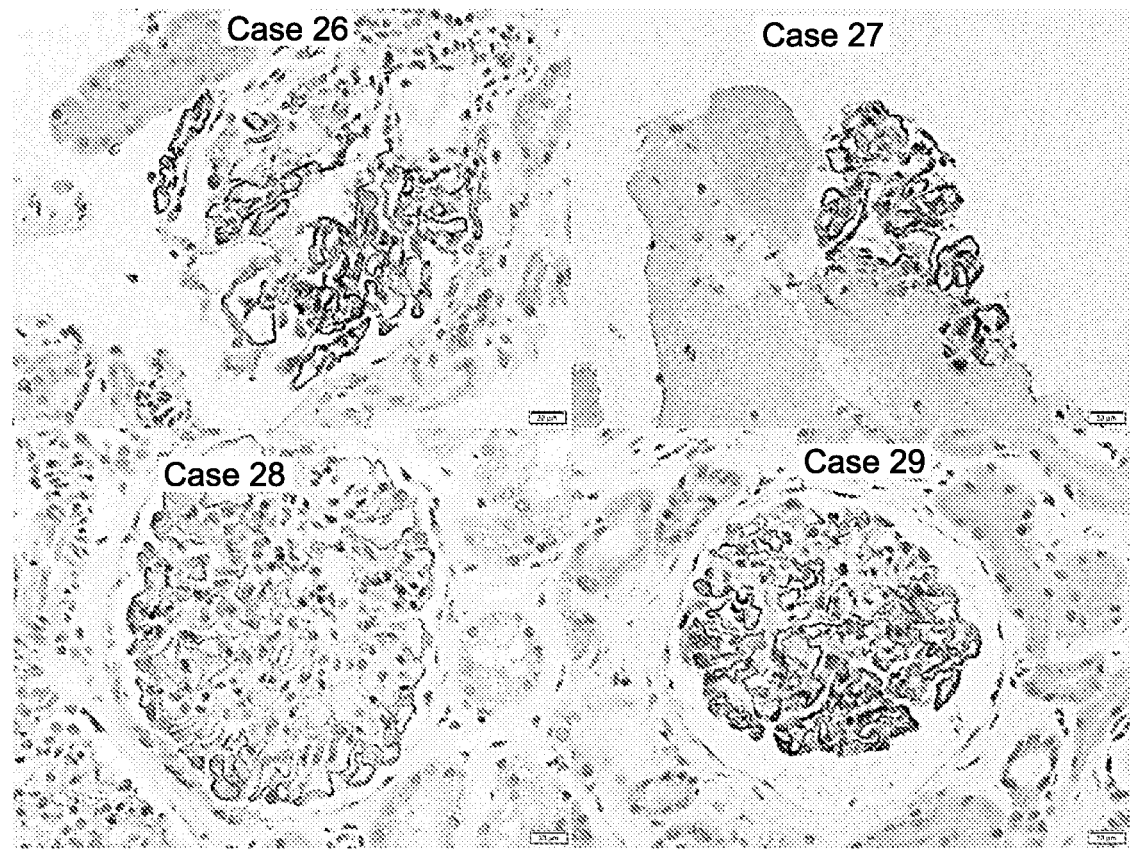

IHC staining was performed for NELL-1 in 126 cases of PLA2R-negative MN from the pilot and discovery cohorts. Twenty-nine (23.0%) cases were positive for NELL-1 (6 in the pilot and 23 in the discovery cohort). All 29 positive cases showed bright (2-3+/3) granular staining for NELL-1 along the GBM. Importantly, there was no significant mesangial staining. NELL-1 staining in 6 cases is shown in FIG. 4A. Segmental granular capillary wall staining for NELL-1 was seen in 6 (20.6%) cases. Review of electron microscopy confirmed the segmental subepithelial deposits in all 6 cases (FIG. 5). There was no staining along the Bowman's capsule, tubular basement membranes or in vessel walls. The positive NELL-1 granular staining mirrored the granular IgG along the GBM seen in each case. All control cases were negative for NELL-1. Representative negative staining for NELL-1 in PLA2R-associated MN, FSGS, IgA nephropathy, and diabetes is shown in FIG. 4B. Representative NELL-1 staining in the remaining NELL-1 positive MN is also shown in FIG. 6.

Validation Cohorts

Five (5.9%) of 90 cases of PLA2R and THSD7A-negative MN were positive for NELL-1 staining in the validation cohorts.

Figure 4C:
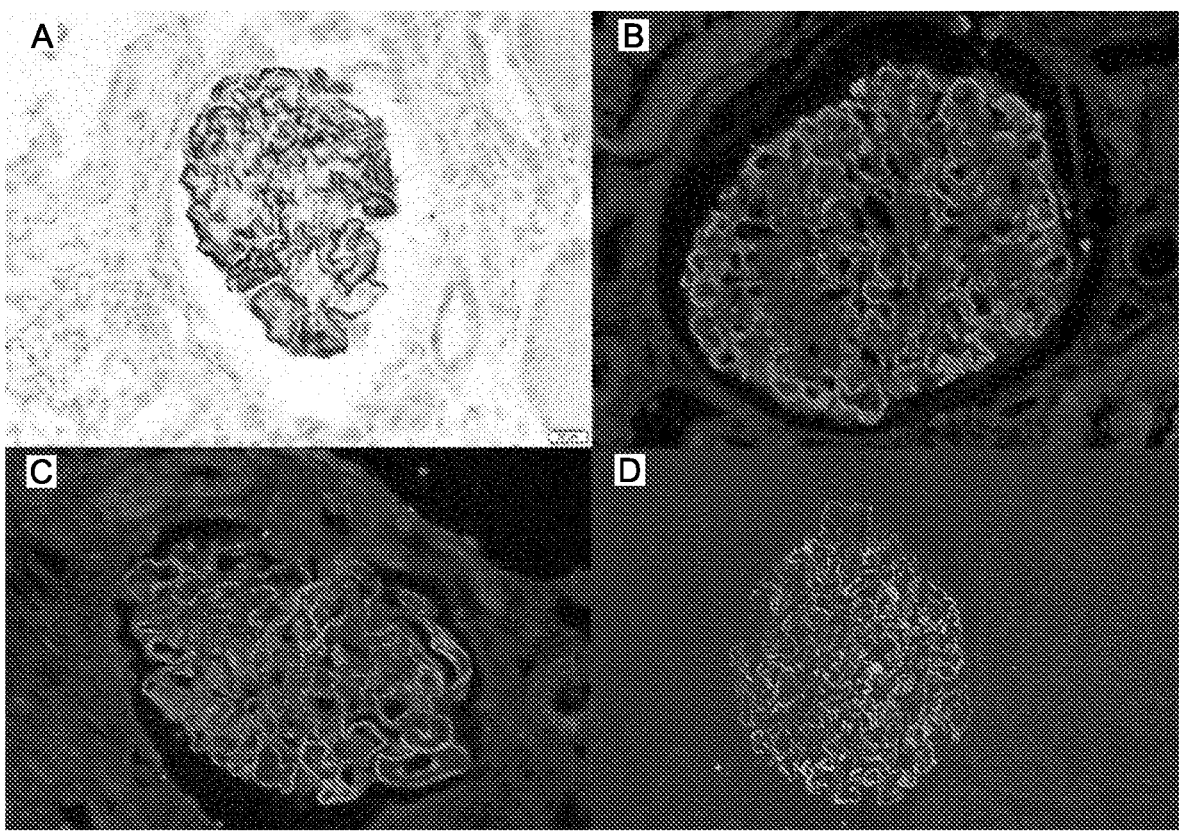

French cohort: Three (6.7%) of 45 cases were positive for NELL-1 staining. Both IHC and immunofluorescence (IF) studies for NELL-1 were done in the first case (patient 30), while IF studies were done for NELL-1 detection in the other 2 cases (patient 31 and 32) (FIG. 4C).

Figure 4D:
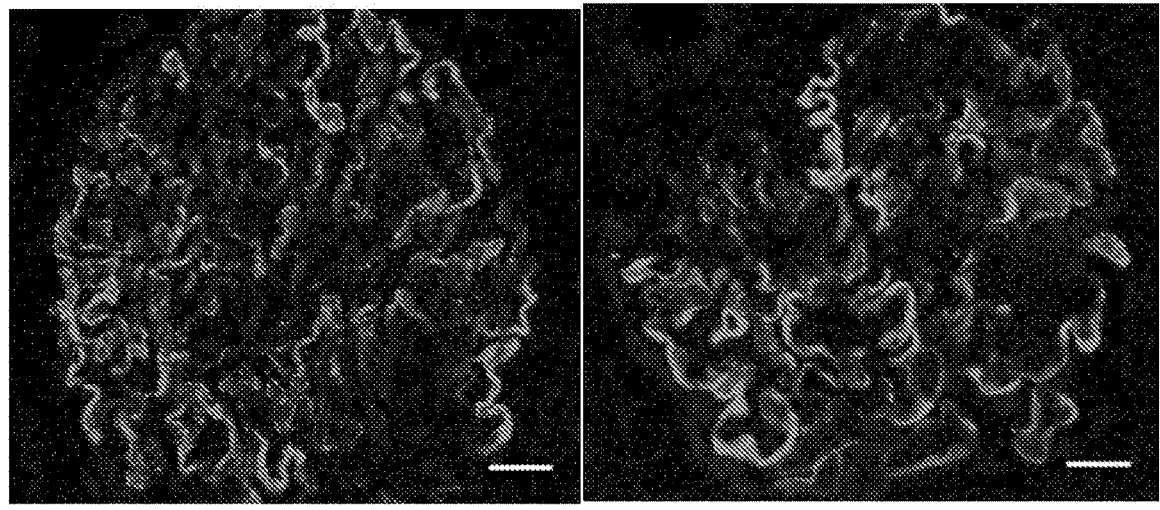

Belgian cohort: Two (5.1%) cases (patients 33 and 34) of 39 cases were positive for NELL-1 staining by IF staining (FIG. 4D).

Confocal Microscopy

Figures 7A, 7B, 7C:
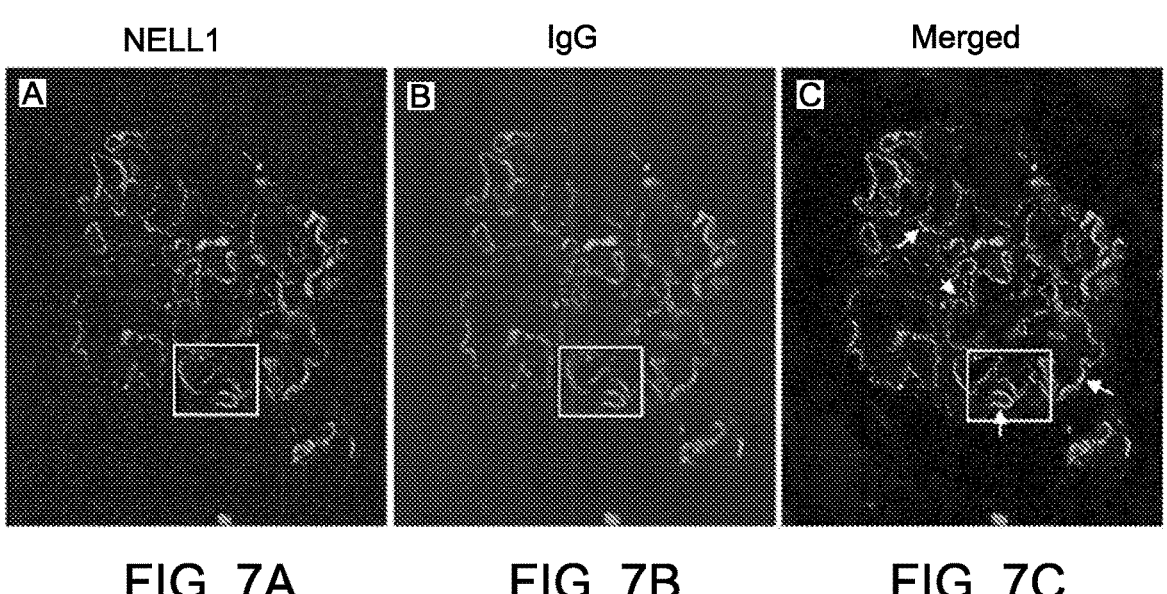
FIGS. 7A-7G. Detection of NELL-1 and IgG in glomerular immune deposits in NELL-1 associated MN by confocal immunofluorescence microscopy analysis. Glomeruli double-labeled with anti-NELL-1 (FIG. 7A) and anti-human IgG (FIG. 7B), the right panel (FIG. 7C) shows the merged image.
Figures 7D, 7E, 7F:
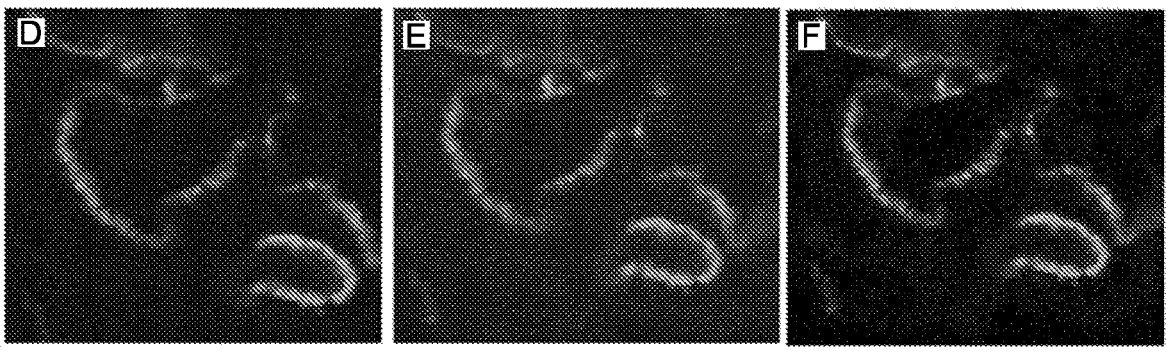
Figure 7G:
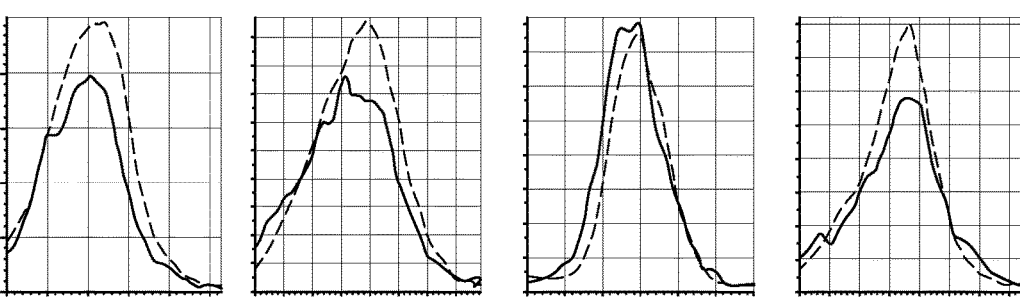
Figures 8A, 8B, 8C:
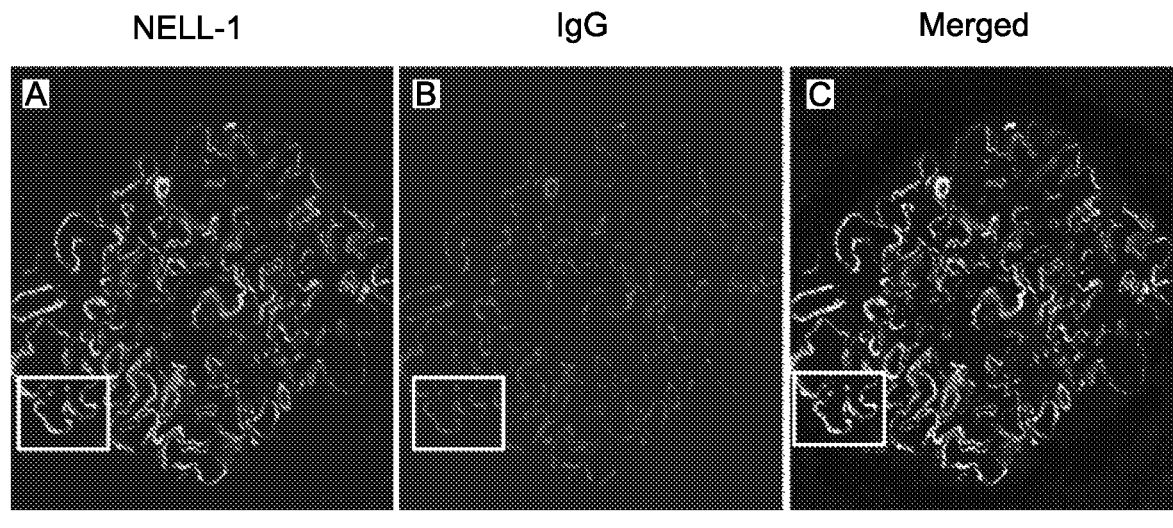
FIGS. 8A-8F. Detection of NELL-1 and IgG in Patient MN2 glomerular immune deposits by confocal microscopy analysis. Glomeruli double-labeled with anti-NELL1 (FIG. 8A) and anti-human IgG (FIG. 8B)
Figures 8D, 8E, 8F:
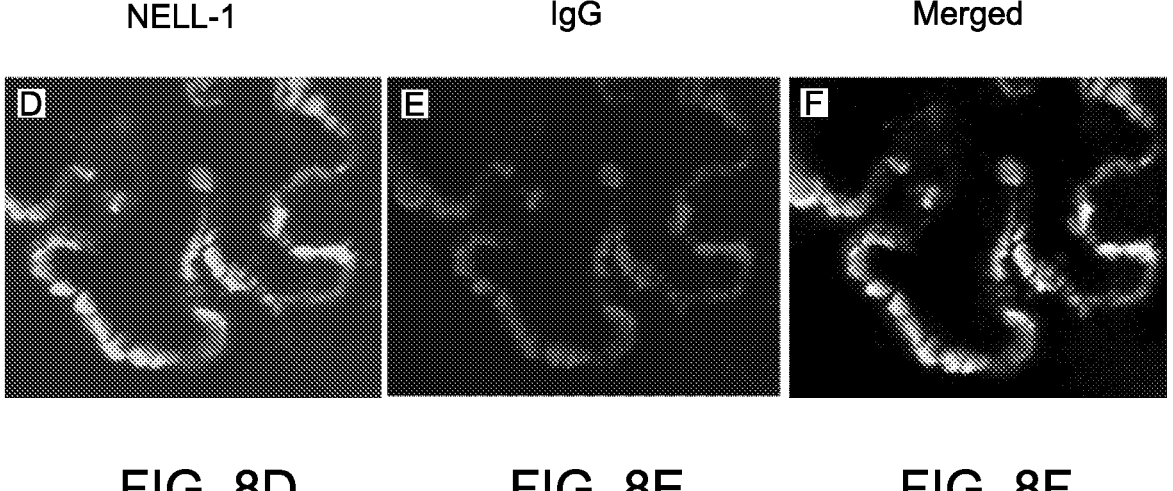

Confocal immunofluorescence microscopy was performed to show that the NELL-1 and IgG co-localize along the GBM (FIG. 7). Superimposition of the two signals (FIGS. 7C, F) and laser quantitative analysis (FIG. 7G) confirm the co-localization of NELL-1 and IgG further corroborating that the subepithelial deposits contain both NELL-1 and IgG. A second case is shown in FIG. 8.

Western Blot Analysis

Figure 9A:
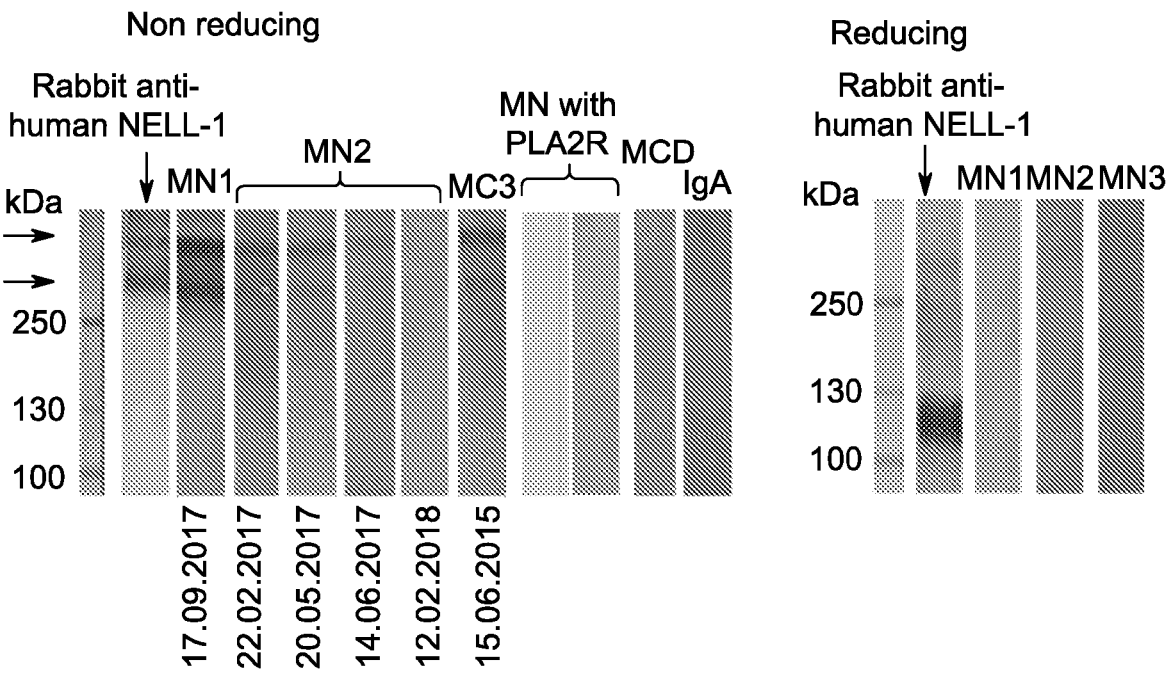
FIGS. 9A-9C.

Western blot analyses were performed using recombinant human NELL-1 to determine the presence of circulating anti-NELL-1 antibodies in the serum of 5 patients—four patients from the validation cohort and one from the discovery cohort. All 5 patients showed reactivity against NELL-1 under non reducing conditions (patients are labeled as MN in the table); NELL-1 was detected as 280 kDa homodimer and 420-kDa homotrimer. Furthermore, sera were available at different points in patient MN2. The MN2 sera were tested both prior and during follow-up (FIG. 9A). Sera from patients with PLA2R-associated MN, minimal change disease and IgA nephropathy did not show any reactivity against NELL-1. There was no reactivity under reducing conditions where NELL-1 resolves as monomeric bands of about 130 kDa, suggesting that NELL-1 autoantibody recognizes conformation dependent epitopes.

Figure 9B:
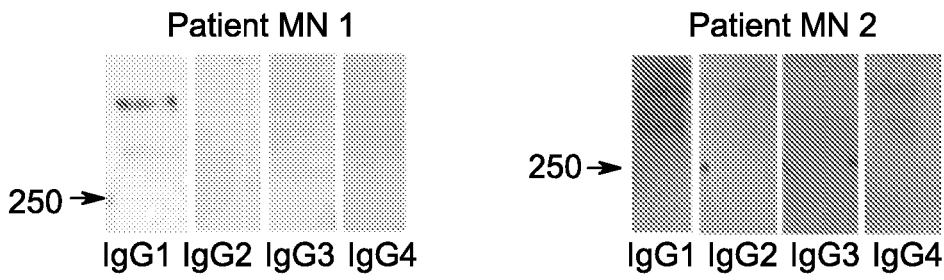
Figure 9C:

Finally, the NELL-1 autoantibodies were characterized and it was shown that the predominant IgG subclass is IgG1 in patient MN1 and MN3, and IgG2 and IgG4 were also present along with IgG1 in MN2 (FIG. 9B).

Clinical and Kidney Biopsy Findings of NELL-1 Associated MN 29 cases of NELL-1-associated MN were identified from the pilot and discovery cohorts (patients 1-29). There were 15 (51.7%) male and 14 (48.3%) female patients. The mean age at presentation was 63.1 (SD±10.4) years. The mean serum creatinine and proteinuria at presentation was 1.7 mg/dL (SD±1.4) and 6.9 g/24 hours (SD±3.4), respectively.

Twenty-four hour urinary protein was not done in 7 patients. With the exception of 1 patient with positive ANA titers, serologies including hepatitis were negative.

The kidney biopsy of all cases of NELL-1 associated MN showed the characteristic findings of thickened GBM on light microscopy, bright IgG and C3 staining along the capillary wall on immunofluorescence microscopy and subepithelial deposits on electron microscopy. Overall, an average of 20.6 (SD±13.7) glomeruli were present of which 3.2 (SD±4.6) were globally sclerosed. Immunofluorescence microscopy showed bright staining for IgG (2-3+/3) and C3 (2-3+/3) in all cases. Only 1 case showed 1+IgA and 1 case showed 1+C1q. The remaining cases were negative for IgA, IgM and C1q. All cases showed staining for kappa (2-3+/3) and lambda (2-3+/3) light chains. Immunofluorescence staining for PLA2R was negative in all cases. Electron microscopy showed subepithelial deposits in all cases, in 6 cases the subepithelial deposits were present in a segmental manner involving some but not all the capillary loops. Subendothelial and mesangial deposits were not present. Tubuloreticular inclusions were not present.

The three positive NELL-1 cases of the French validation cohort were also older patients, two male and one female patient. Interestingly, one (patient 30) had lung cancer (epidermoid type), one (patient 31) had metastatic pancreatic carcinoma, and the third patient (patient 32) had metastatic breast cancer. In all 3 patients of that cohort, cancer was discovered at the time of, or a few months after, the diagnosis of MN. One (patient 33) of the two positive NELL-1 cases of the Belgian validation cohort was young woman while other (patient 34) was an older male patient. Patient 34 developed infiltrating urothelial carcinoma 8 months after diagnosis of MN. The clinical and pathology findings are shown in Table 2.

TABLE 2

| Laboratory and kidney biopsy findings of NELL-1 associated MN. | | | | | | | |
|---|---|---|---|---|---|---|---|
| Case # | Age | Sex | Urinary protein gm/24 hrs | Serum Creatinine mg/dL | Sclerosed/ Total glomeruli | IFTA* | IF | EM |
| 1 (MN5) | 65 | M | 1.5 | 1.7 | 1 scl/12 | 10 | IgG 3+, C1q 1+, C3 2+ | II |
| 2 | 66 | F | 11 | 1.2 | 4 scl/13 | 10 | IgG 3+, C3 1+ | II |
| 3 | 71 | F | NA | 4.0 | 6 scl/33 | 50 | IgG 3+, IgA 1+ | II, seg |
| 4 | 63 | F | NA | 1.1 | 5 scl/23 | 5 | IgG 3+, C3 2+ | II |
| 5 | 66 | F | NA | NA | 1 scl/19 | 0 | IgG 3+, C3 2+ | II-II, seg |
| 6 | 34 | F | 4.4 | 0.6 | 0 scl/26 | 0 | IgG 3+, C3 1+ | II-II |
| 7 | 67 | M | 11.7 | 3 | 6 scl/20 | 10 | IgG 3+, C3 2+ | II |
| 8 | 75 | F | 15 | 1.2 | 2 scl/8 | 10 | IgG 3+, C3 2+ | II |
| 9 | 63 | F | 7.5 | 0.7 | 2 sel/28 | 10 | IgG 3+, C3 3+ | II, seg |
| 10 | 61 | F | 9 | 1.2 | 5 scl/30 | 0 | IgG 3+, C3 2+ | II |
| 11 | 63 | M | 12 | 1.6 | 12 scl/50 | 25 | IgG 3+, C3 2+ | II |
| 12 | 51 | F | 7.1 | 0.6 | 2 scl/30 | 0 | IgG 2+, C3 1+ | I-II |
| 13 | 63 | F | 4 | 1 | 0 scl/5 | 10 | IgG 2+, C3 1+ | II, seg |
| 14 | 67 | M | 5 | 1.2 | 3 scl/11 | 10 | IgG 3+, C3 2+ | I-II |
| 15 | 73 | M | NA | 2.5 | 3 scl/8 | 30 | IgG 2+, C3 1+ | I-II |
| 16 | 75 | F | 3.7 | 0.8 | 2 scl/22 | 10 | IgG 2+, C3 1+ | II |
| 17 | 68 | F | 7 | 0.9 | 0 scl/19 | 10 | IgG 3+, C3 2+ | I |
| 18 | 65 | M | 6 | 1.0 | 3 scl/20 | 25 | IgG 3+, C3 2+ | II, seg |
| 19 | 62 | M | 8.9 | 1.0 | 0 scl/1 | Minimal cortex | IgG 3+, C3 2+ | ND |
| 20 | 55 | F | 4 | 0.6 | 1 scl/18 | 0 | IgG 3+, C3 3+ | I-II |
| 21 | 82 | M | NA | 4.2 | 0 scl/9 | 20 | IgG 3+, C3 3+ | I |
| 22 | 63 | M | NA | 3.2 | 9 scl/32 | 30 | IgG 2+, C3 1+ | II |
| 23 | 56 | M | NA | NA | 22/38 | 40 | IgG 3+, C3 1+ | II |
| 24 | 73 | M | 3 | 1.7 | 2 scl/22 | 0 | IgG 3+, C3 1+ | II-II |
| 25 | 37 | F | 8 | 0.7 | 3 scl/61 | 0 | IgG 3+, C3 1+ | II, seg |
| 26 | 60 | M | 3.1 | 1.2 | 0 scl/18 | 0 | IgG 2+, C3 1+ | I |
| 27 | 66 | M | NA | 4.2 | 0 scl/5 | 0 | IgG 3+, C3 1+ | I |
| 28 | 49 | M | 2.1 | 0.9 | 0 scl/17 | 0 | IgG 2+, C3 1+ | I |
| 29 | 72 | M | 5 | 6.1 | 0 scl/1 | 0 | IgG 2+, C3 2+ | II |

TABLE 2-continued

Laboratory and kidney biopsy findings of NELL-1 associated MN.

| Case # | Age | Sex | Urinary protein gm/24 hrs | Serum Creatinine mg/dL | Sclerosed/Total glomeruli | IFTA* | IF | EM |
|--------|-----|-----|---------------------------|------------------------|---------------------------|-------|-----|-----|
| 30 (MN1) | 78 | M | 4.5 | 1.7 | 4 scl/14 | 20 | IgG 3+, C3+ | II |
| 31 (MN2) | 67 | M | 9.8 | 1.0 | 1 scl/18 | 0 | IgG 3+, C3 3+ | II |
| 32 (MN3) | 71 | F | 12.0 | 0.4 | 1 scl/15 | 10 | IgG 3+ C3 3+ | I |
| 33 (MN4) | 30 | F | 3.7 | 0.6 | 1 scl/11 | <25 | IgG 3+, C3+ | ND |
| 34 | 71 | M | 12.9 | 1.35 | 3 scl/16 | <25 | IgG 3+, C1q 1+ C3 3+, | ND |

Together these results demonstrate that NELL-1 polypeptides are present in a subset of PLA2R-negative MN patients representing distinct type of primary MN. Accordingly, the presence of NELL-1 polypeptides in a sample obtained from a patient (e.g., a human) can be used to identify the mammal as having NELL-1 positive MN.

Example 2: Identifying NELL-1 Positive Membranous Nephropathy

A blood sample (e.g., serum) is obtained from a human having membranous nephropathy. The obtained sample is examined for the presence of autoantibodies specific for a NELL-1 polypeptide.

If autoantibodies specific for a NELL-1 polypeptide are detected in the sample, as compared to a control level, then the human classified as having a NELL-1 positive membranous nephropathy.

Example 3: Treating NELL-1 Positive Membranous Nephropathy

A human identified as having autoantibodies specific for a NELL-1 polypeptide is administered one or more immunosuppressive agents (e.g., corticosteroids, cyclosporine, or a B-cell reduction or depletion agent such as Rituximab).

The administered immunosuppressive agent(s) can reduce inflammation and/or B-cell autoantibody production.

The administered immunosuppressive agent(s) can reduce the level of autoantibodies specific for a NELL-1 polypeptide present within the human.

Example 4: Identifying NELL-1 Positive Membranous Nephropathy

A kidney tissue sample is obtained from a human having membranous nephropathy. The obtained sample is examined for an elevated level of a NELL-1 polypeptide.

If an elevated level of a NELL-1 polypeptide is detected in the sample, as compared to a control level, then the human classified as having a NELL-1 positive membranous nephropathy.

Example 5: Treating NELL-1 Positive Membranous Nephropathy

A human identified as having an elevated level of a NELL-1 polypeptide is administered one or more immunosuppressive agents (e.g., corticosteroids, cyclosporine, or a B-cell reduction or depletion agent such as Rituximab).

The administered immunosuppressive agent(s) can reduce inflammation and/or B-cell autoantibody production.

The administered immunosuppressive agent(s) can reduce a level of autoantibodies specific for a NELL-1 polypeptide present within the human.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating membranous nephropathy, wherein said method comprises administering an immunosuppressant to a mammal identified as having membranous nephropathy and (i) autoantibodies specific for a polypeptide or (ii) kidney tissue comprising an elevated level of said polypeptide, wherein said polypeptide is a neural epidermal growth factor (EGF)-like 1 (NELL-1) polypeptide.

2. The method of claim 1, wherein said mammal is a human.

3. The method of claim 1, wherein said immunosuppressant is selected from the group consisting of a B-cell inhibitor, a calcineurin inhibitor, an mTOR inhibitor, and a DNA damage inducer.

4. The method of claim 3, wherein said B-cell inhibitor is rituximab.

5. The method of claim 3, wherein said calcineurin inhibitor is cyclosporine or tacrolimus.

6. The method of claim 3, wherein said mTOR inhibitor is sirolimus or everolimus.

7. The method of claim 3, wherein said DNA damage inducer is chlorambucil.

8. The method of claim 1, wherein the level of autoantibodies present within said mammal is reduced by at least 5 percent following said administering step.

9. A method for detecting (i) a presence or absence of autoantibodies specific for a polypeptide or (ii) a presence or absence of kidney tissue comprising an elevated level of said polypeptide in a sample of said kidney tissue from said mammal, wherein said polypeptide is a neural epidermal growth factor (EGF)-like 1 (NELL-1) polypeptide, in a sample of a mammal having or suspected of having membranous nephropathy.

10. The method of claim 9, wherein said mammal is a human.

11. The method of claim 9, wherein said mammal has the presence of said autoantibodies or the presence of said kidney tissue comprising the elevated level of said polypeptide, and said method comprises administering an immunosuppressant to said mammal.

12. The method of claim 11, wherein said immunosuppressant is selected from the group consisting of a B-cell inhibitor, a calcineurin inhibitor, an mTOR inhibitor, and a DNA damage inducer.

13. The method of claim 12, wherein said B-cell inhibitor is rituximab.

14. The method of claim 12, wherein said calcineurin inhibitor is cyclosporine or tacrolimus.

15. The method of claim 12, wherein said mTOR inhibitor is sirolimus or everolimus.

16. The method of claim 12, wherein said DNA damage inducer is chlorambucil.

17. The method of claim 11, wherein the level of autoantibodies present within said mammal is reduced by at least 5 percent following said administering step.

* * * * *